US011744860B2

(12) United States Patent
Taniguchi et al.

(10) Patent No.: US 11,744,860 B2
(45) Date of Patent: Sep. 5, 2023

(54) TECHNOLOGY FOR EFFICIENT ACTIVATION OF NKT CELLS

(71) Applicants: RIKEN, Wako (JP); AMBICION CO., LTD., Tokyo (JP)

(72) Inventors: Masaru Taniguchi, Wako (JP); Tomokuni Shigeura, Wako (JP); Minako Aihara, Wako (JP); Keigo Hanada, Tokyo (JP)

(73) Assignees: RIKEN, Wako (JP); AMBICION CO., LTD., Tokyo (JP)

( * ) Notice: Subject to any disclaimer, the term of this patent is extended or adjusted under 35 U.S.C. 154(b) by 538 days.

(21) Appl. No.: 16/096,561

(22) PCT Filed: Apr. 14, 2017

(86) PCT No.: PCT/JP2017/015383
§ 371 (c)(1),
(2) Date: Oct. 25, 2018

(87) PCT Pub. No.: WO2017/188033
PCT Pub. Date: Nov. 2, 2017

(65) Prior Publication Data
US 2019/0134094 A1 May 9, 2019

(30) Foreign Application Priority Data
Apr. 28, 2016 (JP) ................. 2016-091674

(51) Int. Cl.
*A61K 35/17* (2015.01)
*A61P 35/00* (2006.01)
*C12N 5/0783* (2010.01)

(52) U.S. Cl.
CPC .............. *A61K 35/17* (2013.01); *A61P 35/00* (2018.01); *C12N 5/0646* (2013.01)

(58) Field of Classification Search
CPC ........ A61K 35/17; A61P 35/00; C12N 5/0646
See application file for complete search history.

(56) References Cited

U.S. PATENT DOCUMENTS

| 2004/0009594 | A1 | 1/2004 | Wakasugi |
| 2009/0104161 | A1 | 4/2009 | Nieda et al. |
| 2009/0233323 | A1 | 9/2009 | Fujii et al. |
| 2009/0285851 | A1 | 11/2009 | Kang et al. |
| 2010/0062990 | A1 | 3/2010 | Tashiro et al. |
| 2011/0104188 | A1 | 5/2011 | Tashiro et al. |
| 2011/0244158 | A1 | 10/2011 | Murakami et al. |
| 2013/0005669 | A1 | 1/2013 | Tashiro et al. |
| 2015/0071960 | A1 | 3/2015 | Wong et al. |
| 2015/0152128 | A1 | 6/2015 | Tashiro et al. |

FOREIGN PATENT DOCUMENTS

| CN | 1444648 A | 9/2003 |
| CN | 101258238 A | 9/2008 |
| WO | WO 2008/102888 A1 | 8/2008 |
| WO | WO 2009/119692 A1 | 10/2009 |
| WO | WO 2010/030012 A1 | 3/2010 |
| WO | WO 2011/096536 A1 | 8/2011 |
| WO | WO 2013/162016 A1 | 10/2013 |

OTHER PUBLICATIONS

Kasinrerk et al., "CD1 molecule expression on human monocytes induced by granulocyte-macrophage colony-stimulating factor," J. Immunol., 150: 579-584 (1993).
European Patent Office, Supplementary European Search Report in European Patent Application No. 17789318 (dated Nov. 29, 2019).
Asada-Mikami et al., "Increased expansion of Vα24+ T cells derived from G-CSF-mobilized peripheral blood stem cells as compared to peripheral blood mononuclear cells following α-galactosylceramide stimulation," Cancer Sci., 94(4): 383-388 (2003).
Burdin et al., "Selective Ability of Mouse CD1 to Present Glycolipids: α-Galactosylceramide Specifically Stimulates Vα14+ NK T Lymphocytes," J. Immunol., 161(7): 3271-3281 (1998).
Cui et al., "Requirement for $V_\alpha 14$ NKT Cells in IL-12-Mediated Rejection of Tumors," Science, 278(5343): 1623-1626 (1997).
Fujii et al., "Prolonged IFN-γ-producing NKT response induced with α-galactosylceramide-loaded DCs," Nat. Immunol., 3(9): 867-874 (2002).
Kawano et al., "CD1d-Restricted and TCR-Mediated Activation of $V_\alpha 14$ NKT Cells by Glycosylceramides," Science, 278(5343): 1626-1629 (1997).
Kawano et al., "Natural killer-like nonspecific tumor cell lysis mediated by specific ligand-activated Vα14 NKT cells," Proc. Natl. Acad. Sci. U.S.A., 95(1): 5690-5693 (1998).
Kawano et al., "Antitumor Cytotoxicity Mediated by Ligand-activated Human Vα24 NKT Cells," Cancer Res., 59(20): 5102-5105 (1999).
Motohashi et al., "A Phase I Study of In vitro Expanded Natural Killer T Cells in Patients with Advanced and Recurrent Non-Small Cell Lung Cancer," Clin. Cancer Res., 12(20 Pt. 1): 6079-6086 (2006).
Motohashi et al., "Clinical applications of natural killer T cell-based immunotherapy for cancer," Cancer Sci., 99(4): 638-645 (2008).

(Continued)

*Primary Examiner* — Elly-Gerald Stoica
(74) *Attorney, Agent, or Firm* — Leydig, Voit & Mayer, Ltd.

(57) ABSTRACT

The present invention relates to a method for producing en NKT cell ligand-pulsed human CD14 positive cell that activates NKT cells and strongly induces proliferation, IFN-γ production, and/or cytotoxic activity of NKT cells. More specifically, the method is characterized in that the isolated CD14 positive cell is cultured in a medium containing an NKT cell ligand and GM-CSF and substantially free of IL-4. In addition, the present invention relates to a method for producing an NKT cell ligand-pulsed human CD14 positive cell line and, specifically, the method is characterized in that the isolated CD14 positive cell is cultured in a medium containing an NKT cell ligand and substantially free of GM-CSF and IL-4. The present invention also relates to a cell preparation containing an NKT cell ligand-pulsed human CD14 positive cell or an NKT cell ligand-pulsed human CD14 positive cell line and pharmaceutical use thereof.

14 Claims, 25 Drawing Sheets

(56) References Cited

OTHER PUBLICATIONS

Motohashi et al., "A Phase I-II Study of α-Galactosylceramide-Pulsed IL-2/GM-CSF-Cultured Peripheral Blood Mononuclear Cells in Patients with Advanced and Recurrent Non-Small Cell Lung Cancer," *J. Immunol.*, 182(4): 2492-2501 (2009).

Spada et al., "CD1d-restricted Recognition of Synthetic Glycolipid Antigens by Human Natural Killer T Cells," *J. Exp. Med.*, 188(8): 1529-1534 (1998).

Spada et al., "Low expression level but potent antigen presenting function of CD1d on monocyte lineage cells," *Eur. J. Immunol.*, 30(12): 3468-3477 (2000).

Taniguchi et al., "The NKT cell system: bridging innate and acquired immunity," *Nat. Immunol.*, 4(12): 1164-1165 (2003).

Toura et al., "Cutting Edge: Inhibition of Experimental Tumor Metastasis by Dendritic Cells Pulsed with α-Galactosylceramide," *J. Immunol.*, 163(5): 2387-2391 (1999).

Watanabe et al., "Relationships Between Intermediate TCR Cells and NK1.1+ Cells in Various Immune Organs: NK1.1+ T Cells Are Present Within a Population of Intermediate TCR Cells," *J. Immunol.*, 155(6): 2972-2983 (1995).

Japanese Patent Office, International Search Report in International Patent Application No. PCT/JP2017/015383 (dated Jul. 4, 2017).

China National Intellectual Property Administration, Search Report in Chinese Patent Application No. 201780040540.4 (dated Nov. 25, 2021).

FIG. 1
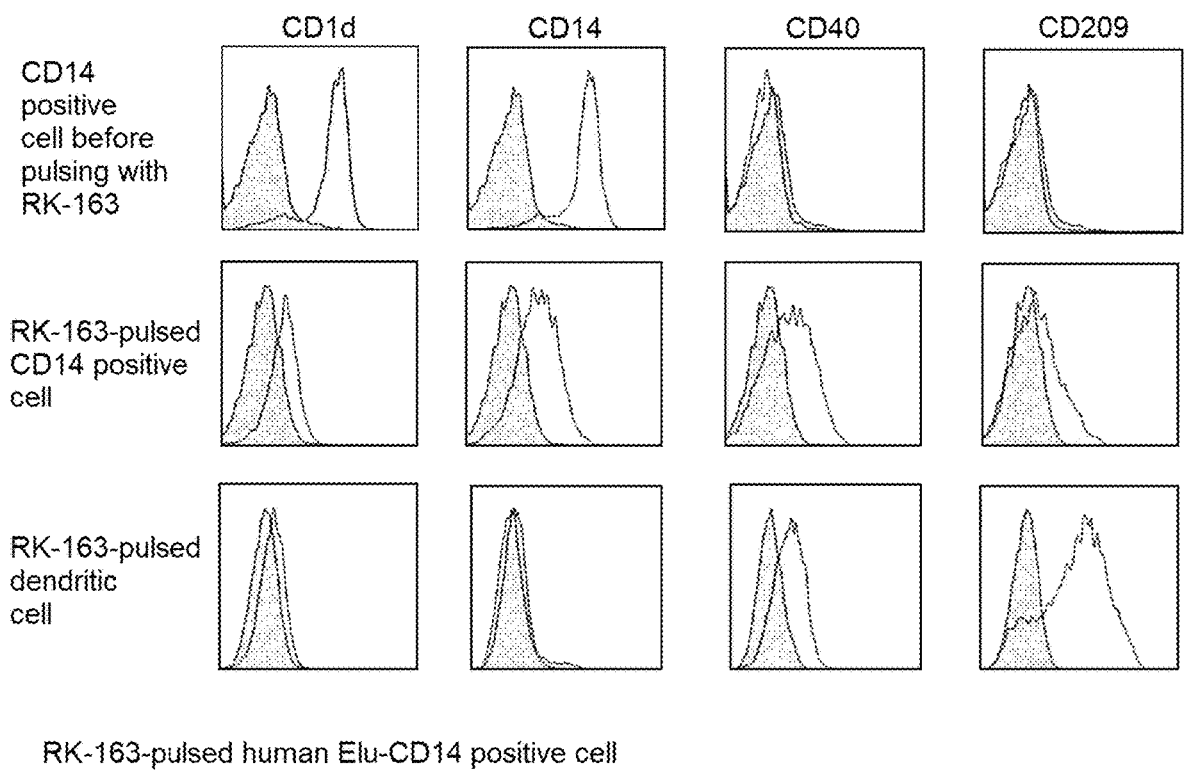
RK-163-pulsed human Elu-CD14 positive cell
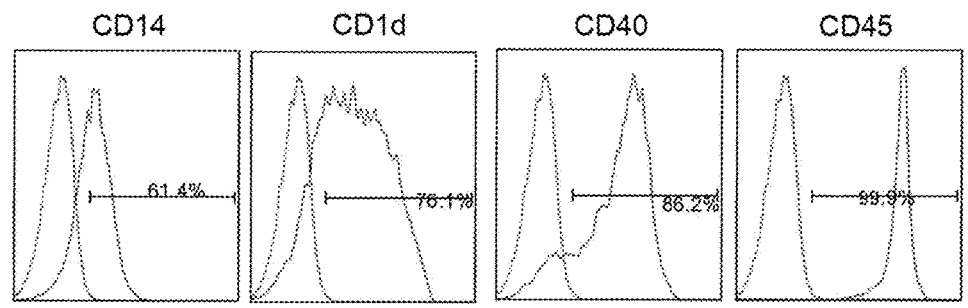

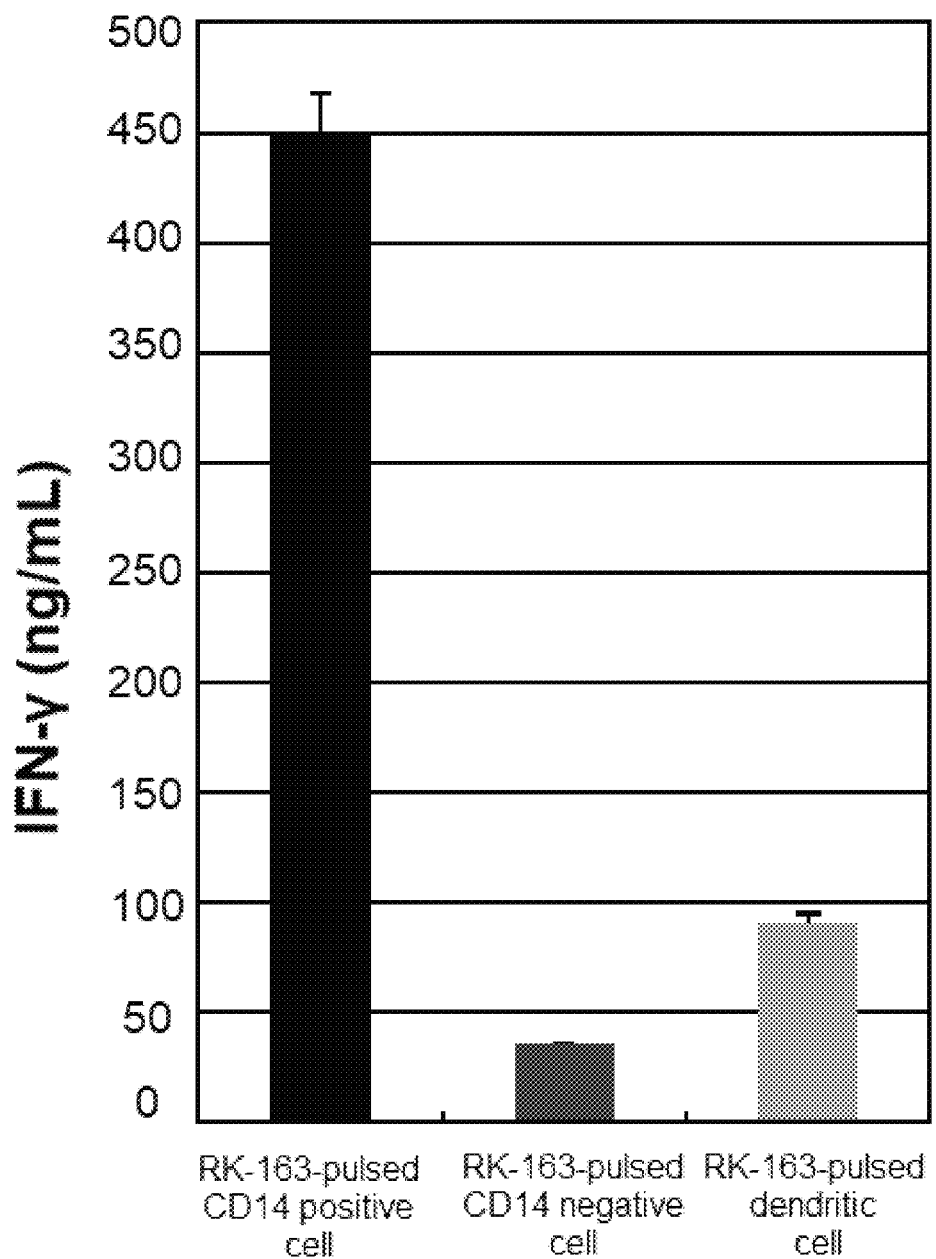

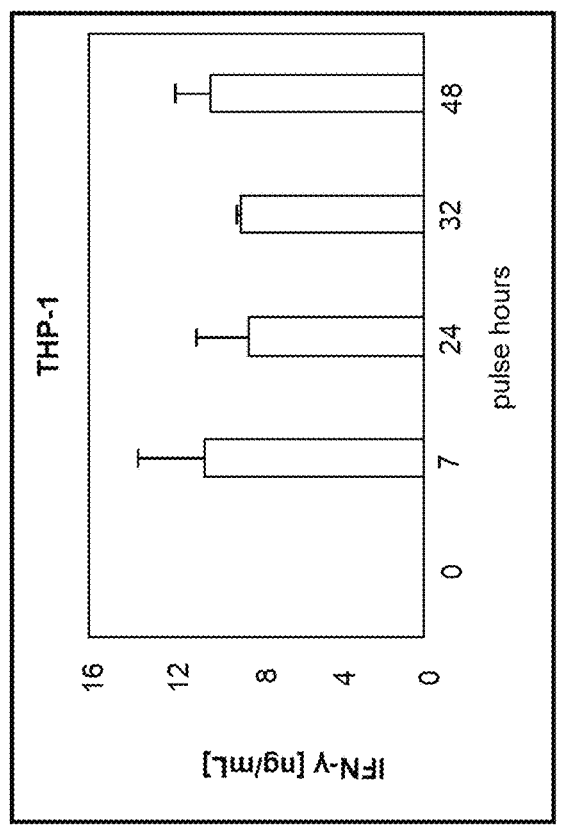
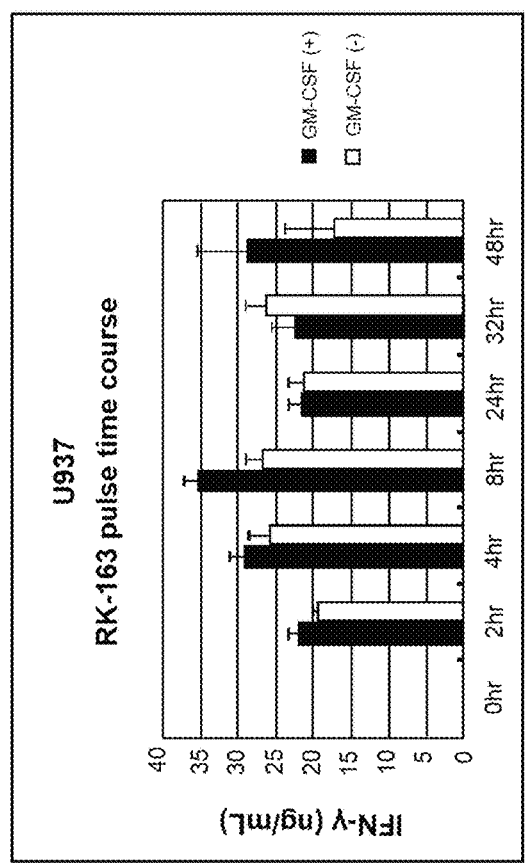
FIG. 12

FIG. 14B
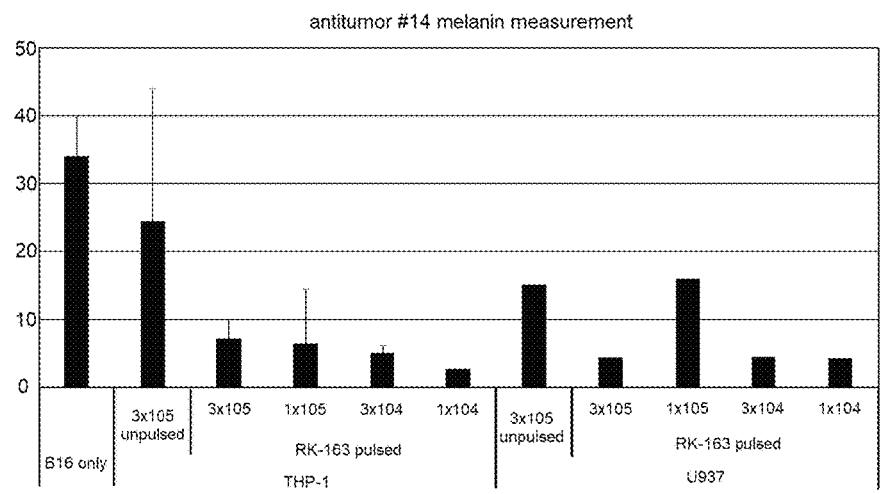
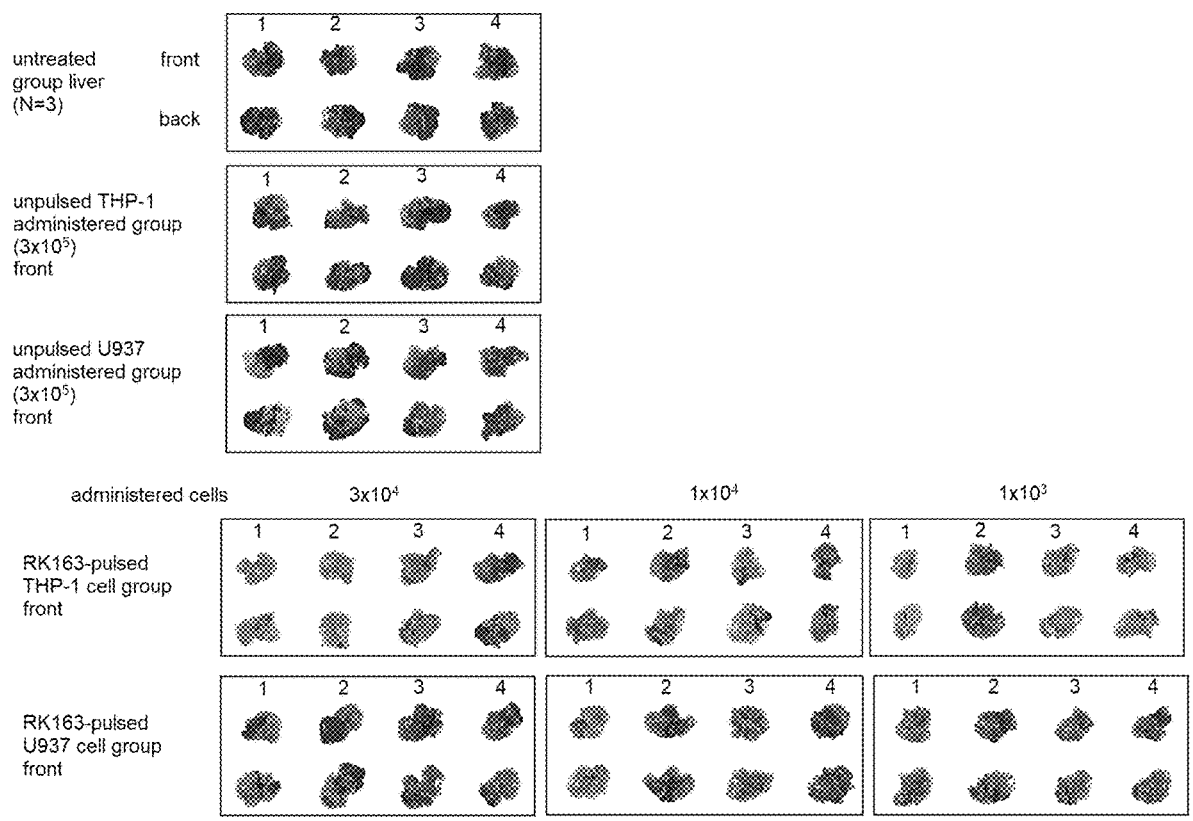

——— RK-163 pulse
——— unpulse

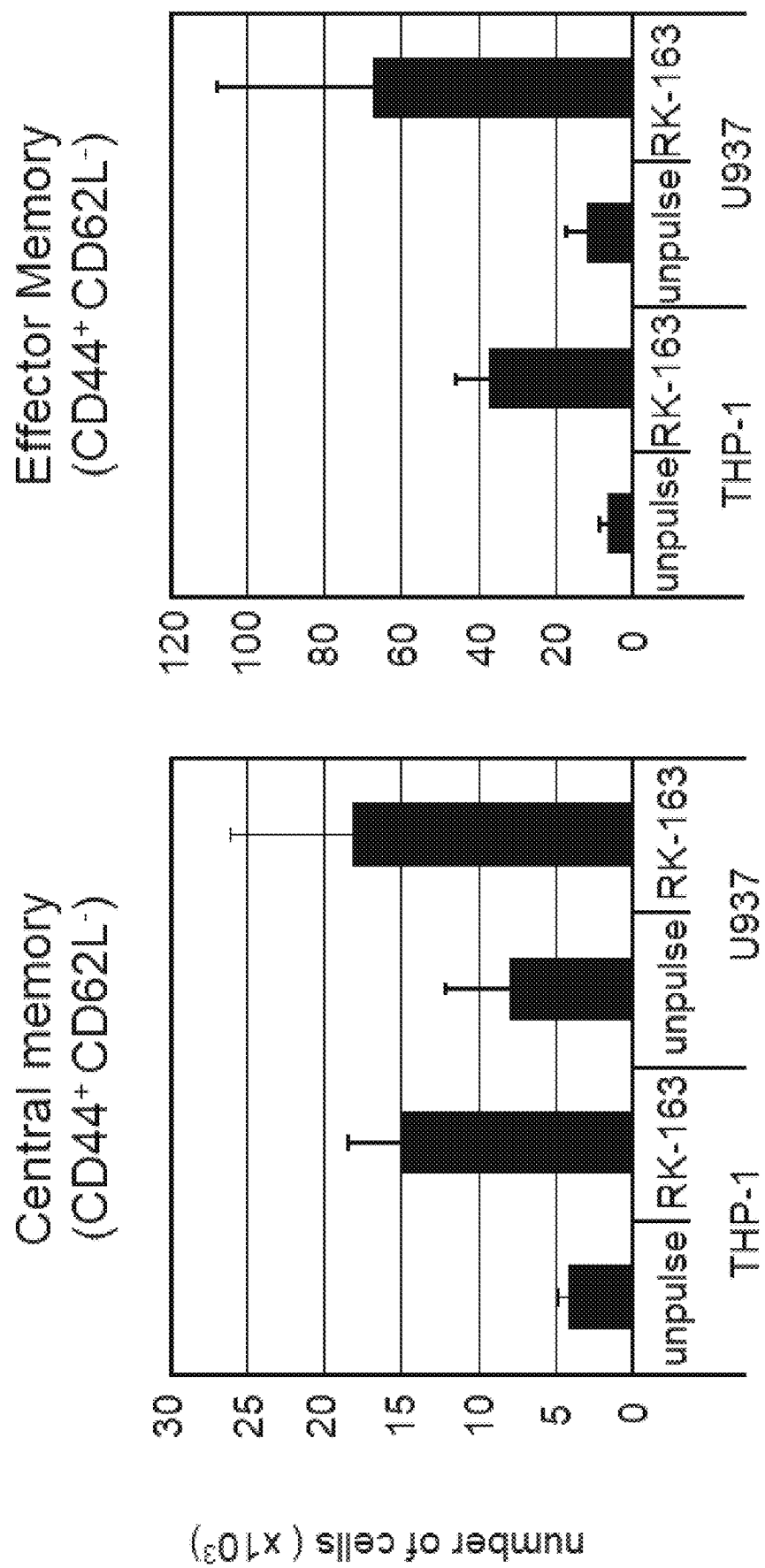

TECHNOLOGY FOR EFFICIENT ACTIVATION OF NKT CELLS

CROSS-REFERENCE TO RELATED APPLICATIONS

This patent application is the U.S. national phase of International Patent Application No. PCT/JP2017/015383, filed Apr. 14, 2017, which claims the benefit of Japanese Patent Application No. 2016-091674, filed on Apr. 28, 2016, which are incorporated by reference in their entireties herein.

TECHNICAL FIELD

The present invention relates to a technique for efficient activation of NKT cells. More specifically, the present invention relates to a method for producing NKT cell ligand-pulsed cells having a superior NKT cell activation activity, cells obtained by the method, pharmaceutical use of the cells and the like.

BACKGROUND ART

Natural killer (hereinafter NK) T cell is an immunocyte belonging to a novel lymphocyte lineage and showing characteristics different from those of other lymphocyte lineages (T, B, NK cells). NKT cell is related to NK cell since cytotoxic perforin granules are present in the NKT cell (non-patent document 1). However, since NKT cell expresses not only NK cell marker but also T cell receptor (TCR), it is a definitely different new cell population (non-patent document 2). NKT cell has the capacity to produce both Th-1 type cytokines (mainly IFN-γ) and Th-2 type cytokines (mainly IL-4) (non-patent document 3) and it is thus suggested that NKT cell possibly plays a role in balancing the immune system (non-patent document 4). Therefore, if the action of NKT cell can be controlled, various diseases caused by the balance abnormality of the immune system, particularly cancer and infectious diseases, can be treated.

The most notable property of NKT cell is that the α chain of TCR expressed in NKT cell is identical among all individuals of one species. This indicates that all NKT cells in allogenic organisms are activated by recognition of the same substance. This α chain is Vα24 in human and Vα14 in mouse, and it has very high homology between the two species. In addition, only very limited kinds of β chains are known to pair with a chain. Therefore, this TCR is also called "invariant TCR". It is also characteristic that TCR of NKT cell recognizes glycolipids while TCR of general T cell recognizes protein fragments.

α-Galactosylceramide (α-GalCer) is a glycolipid isolated from the extract of Agelas mauritianus which is one kind of marine sponge and was reported to strongly activate NKT cells (non-patent document 5). α-Galactosylceramide is taken up by antigen presenting cells (APC) typified by dendritic cell (DC) and the like and then presented on the cell membrane by the CD1d protein similar to the major histocompatibility complex (MHC) class I molecule. Since only one kind of this CD1d molecule exists in the species and is common to all people, α-GalCer becomes a drug common to all human beings. NKT cell is activated by recognition of the thus-presented complex of CD1d protein and α-galactosylceramide by using the sole TCRα chain in NKT cell and initiates various immune reactions In recent years, the function of NKT cell as described above has been noted and therapeutic drugs for cancers containing α-GalCer as an active ingredient have been developed. However, NKT cell activated by administration of α-GalCer produces IFN-γ (a cytokine that stimulates cell-mediated immunity and is useful for treating cancers and infectious diseases), and IL-4 at the same time, which is suppressive to cellular immunity. As a result, the functions of both cancel each other, leading to a possibility pointed out that the effect on the treatment of cancers and infectious diseases may not always be sufficient.

Therefore, many α-GalCer derivatives have been developed that strongly activate NKT cells and produce IFN-γ preferentially over IL-4 (patent documents 1-5).

NKT cells activated by α-GalCer directly shows cytotoxic activity against target cells by expressing various cytocidal inducers such as perforin and the like (non-patent documents 1, 6). They are very unique cells in that they exhibit an enhancing effect on the cytotoxic activity of NK cells and CD8+ T cells through Th1-type cytokine such as interferon-γ and the like produced rapidly and in large quantities by activated NKT cells, maturation of dendritic cell (DC) and the like (non-patent document 7). Furthermore, it was revealed in a mouse cancer metastasis model that a more potent antitumor effect is exerted by a cell therapy in which α-GalCer is administered through presentation by dendritic cells (DC) rather than administration of α-GalCer alone (non-patent document 8). Based on these studies, clinical development of immune cell therapy targeting NKT cell has been performed in which DC pulsed with NKT cell ligand such as α-GalCer and the like is administered to activate NKT cells in vivo and the antitumor effect thereof is utilized to treat and prevent cancers and infectious diseases.

For example, non-patent document 9 has reported that, in α-GalCer-pulsed DC therapy for non-small cell lung cancer, a group of cases in which IFN-γ producing cells in peripheral blood cells increased by administration of α-GalCer-pulsed DC showed a significant prolongation of the overall survival period as compared to a non-increase case group. While α-GalCer reactive IFN-γ producing cells are generally NKT cells, it has been found that NK cells are added after administration of α-GalCer-pulsed DC (non-patent documents 10, 11), and an adjuvant effect of NKT cells activated by α-GalCer-pulsed DC therapy on other immune cells is suggested. Given the close relationship between the increase in IFN-γ-producing cells and the survival period prolonging effect, how to enhance IFN-γ production is considered to be important for improving the outcome of the treatment and prevention of cancers and infectious diseases by immune cell therapy using antigen-presenting cells pulsed with NKT cell ligand such as α-GalCer and the like.

In the α-GalCer-pulsed DC therapy in non-patent document 9, dendritic cells are obtained by culturing all the peripheral blood cells, collected from patient by component blood sampling, in the presence of GM-CSF and IL-2 for 1 to 2 weeks. Further, the day before administration to the patient, the dendritic cells are pulsed with α-GalCer, cultured for 1 day, and the obtained α-GalCer-pulsed DC is administered intravenously by drip infusion. In this culture system, maturation of monocyte-derived DC proceeds due to IL-4, TNF-α produced by the T cells contained in the cultured cells, and the α-GalCer presenting ability is enhanced.

Generally, immature dendritic cells are obtained by culturing monocytes in the peripheral blood for about 6 days in the presence of GM-CSF and IL-4, the immature dendritic cells are cultured for about 2 days together with inflammatory cytokines (TNF-α, IL-1β, IL-6) to give mature dendritic cells, and the mature dendritic cells are pulsed with NKT cell ligands such as α-GalCer and the like, whereby NKT cells are activated (non-patent documents 5, 12).

As described above, mature dendritic cells are used exclusively as antigen presenting cells to NKT cells, and monocytes and immature dendritic cells were considered to be incapable of appropriately presenting antigens to NKT cells and efficiently activating the NKT cells. On the other hand, preparation of mature dendritic cells requires culturing for a long term.

DOCUMENT LIST

Patent Documents patent document 1: WO 2008/102888 A1
patent document 2: WO 2009/119692 A1
patent document 3: WO 2010/030012 A1
patent document 4: WO 2011/552842 A1
patent document 5: WO 2013/162016 A1

Non-Patent Documents non-patent document 1: Proc. Natl. Acad. Sci. USA 1998, 95, 5690-5693
non-patent document 2: J. Immunol. 1995, 155, 2972-2983
non-patent document 3: J. Immunol. 1998, 161, 3271-3281
non-patent document 4: Science, 1997, 278, 1623-1626
non-patent document 5: Science, 1997, 278, 1626-1629
non-patent document 6: Cancer Res 1999; 59: 5102-5105
non-patent document 7: Nat Immunol 2003; 4: 1164-1165
non-patent document 8: J Immunol 1999; 163: 2387-2391
non-patent document 9: J Immunol 2009; 182: 2492-2501
non-patent document 10: Clin Cancer Res 2006; 12: 6079-6086
non-patent document 11: Cancer Sci 2008; 99: 638-645.
non-patent document 12: Nat Immunol, 2002, 3(9): 867-874

SUMMARY OF THE INVENTION

Problems to be Solved by the Invention

An object of the present invention is to provide a technique for producing NKT cell ligand-pulsed cells having strong NKT cell activating capacity in a relatively short period.

Means of Solving the Problems

The present inventors have conducted intensive studies in an attempt to solve the aforementioned problem. As a result, they reversed the common knowledge of "antigen presentation by dendritic cells and activation of T cells thereby", and found that monocytes in an embryologically undifferentiated stage, that is, CD14 positive cells, are superior to dendritic cells as antigen presenting cells and pulsed cells when NKT cells are activated. They showed that cultivation of the CD14 positive cells in a medium containing only NKT cell ligand and GM-CSF in the absence of IL-4 increases expression of CD40 necessary for activation of NKT cells and affords NKT cell ligand-pulsed cells capable of strongly activating NKT cells. In the case of monocyte and a CD14 positive cell line that has been established from CD14 positive cell, NKT cell ligand-pulsed CD14 positive cell line can be obtained by culturing in a medium containing NKT cell ligand alone in the absence of GM-CSF and IL-4. In both production steps, a sufficient incubation period was about 2 days. This indicates that a step of differentiating CD14 positive cells into dendritic cells is not necessary and that NKT cell ligand-pulsed cells are obtained directly from the isolated CD14 positive cells or CD14 positive cell lines. The acquired NKT cell ligand-pulsed cell (NKT cell ligand-pulsed CD14 positive cell or NKT cell ligand-pulsed CD14 positive cell line) strongly induced proliferation of NKT cells, IFN-γ production and cytotoxic activity by NKT cells.

The inventors have further studied based on the above-mentioned findings and completed the present invention.

Accordingly, the present invention provides the following:

[1] A method for producing an NKT cell ligand-pulsed cell (i.e., NKT cell ligand-pulsed CD14 positive cell or NKT cell ligand-pulsed CD14 positive cell line), comprising a step of culturing a CD14 positive cell isolated from human peripheral blood in a medium containing an NKT cell ligand and GM-CSF and substantially free of IL-4 (production method 1) or a step of culturing an isolated CD14 positive cell line in a medium containing an NKT cell ligand and substantially free of GM-CSF and IL-4 (production method 2).

[2] The method of [1], wherein the medium is substantially free of SCF and/or Flt3L.

[3] The method of [1] or [2], wherein the isolated CD14 positive cell has a purity of not less than 70%.

[4] The method of any of [1] to [3], wherein the cells are cultured at least for 16 hr after addition of the NKT cell ligand.

[5] The method of [4], wherein the cells are cultured for 16-72 hr after addition of the NKT cell ligand.

[6] The method of any of [1] to [5], wherein the NKT cell ligand is a compound represented by the following formula (VI):

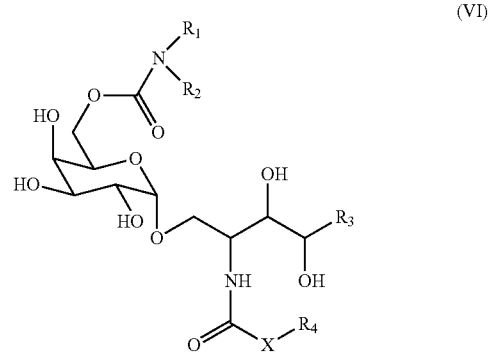

wherein
X is an alkylene group or —NH—;
$R_1$ and $R_2$ are the same or different and each is a hydrogen atom, an alkyl group, a hydroxyl group, an alkoxy group, or an aryl group optionally having a substituent, $R_1$ and $R_2$ optionally form, together with the adjacent nitrogen atom, a 5- or 6-membered ring;
$R_3$ is a hydrocarbon group having 1-20 carbon atoms; and
$R_4$ is a hydrocarbon group having 1-30 carbon atoms, or a salt thereof.

[7] The method of [6], wherein the NKT cell ligand is a compound represented by the following formula

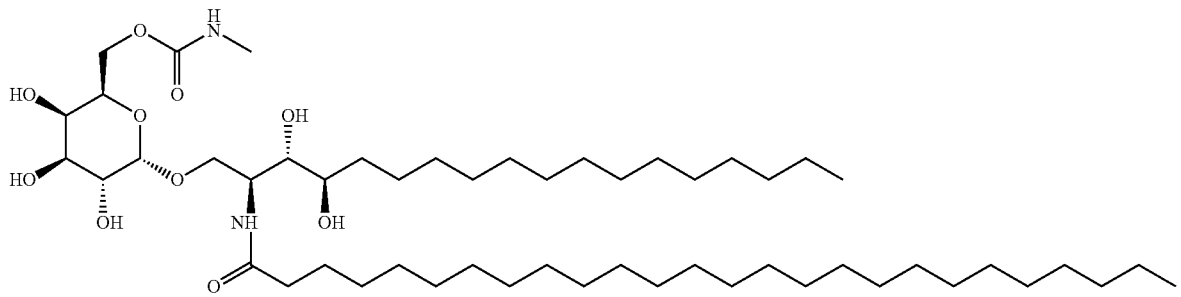 [SMILES: CCCCCCCCCCCCCCCCCCCCCCCCCC(=O)N[C@@H](CO[C@H]1O[C@H](COC(=O)NC)[C@H](O)[C@H](O)[C@H]1O)[C@H](O)[C@H](O)CCCCCCCCCCCCCC]

or a salt thereof.

[8] The method of any of [1] to [7], wherein a concentration of the NKT cell ligand in the medium is at least 30 ng/ml.

[9] A method for producing an NKT cell ligand-pulsed cell (NKT cell ligand-pulsed CD14 positive cell or NKT cell ligand-pulsed CD14 positive cell line), comprising a step of culturing a CD14 positive cell in a medium containing an NKT cell ligand and GM-CSF and substantially free of IL-4 (production method 1) or a step of culturing a CD14 positive cell line in a medium containing an NKT cell ligand and substantially free of GM-CSF and IL-4 (production method 2).

[10] The method of [9], wherein the medium is substantially free of SCF and/or Flt3L.

[11] The method of [9] or [10], wherein the cells are cultured at least for 16 hr after addition of the NKT cell ligand.

[12] The method of [11], wherein the cells are cultured for 40-72 hr after addition of the NKT cell ligand.

[13] The method of any of [9] to [12], wherein the NKT cell ligand is a compound represented by the following formula (VI):

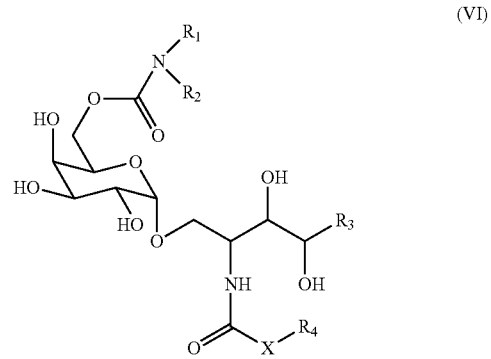

wherein
X is an alkylene group or —NH—;
$R_1$ and $R_2$ are the same or different and each is a hydrogen atom, an alkyl group, a hydroxyl group, an alkoxy group, or an aryl group optionally having a substituent, $R_1$ and $R_2$ optionally form, together with the adjacent nitrogen atom, a 5- or 6-membered ring;
$R_3$ is a hydrocarbon group having 1-20 carbon atoms; and
$R_4$ is a hydrocarbon group having 1-30 carbon atoms, or a salt thereof.

[14] The method of [13], wherein the NKT cell ligand is a compound represented by the following formula

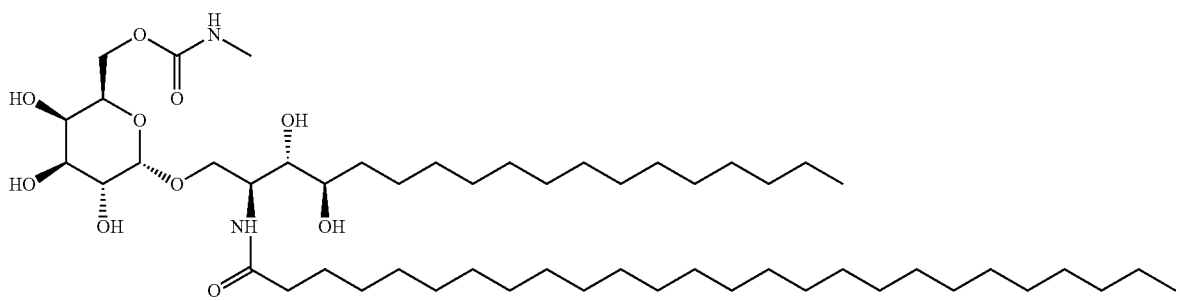 [SMILES: CCCCCCCCCCCCCCCCCCCCCCCCCC(=O)N[C@@H](CO[C@H]1O[C@H](COC(=O)NC)[C@H](O)[C@H](O)[C@H]1O)[C@H](O)[C@H](O)CCCCCCCCCCCCCC]

or a salt thereof.

[15] The method of any of [9] to [14], wherein a concentration of the NKT cell ligand in the medium is at least 30 ng/ml.
[16] An NKT cell ligand-pulsed cell obtained by the method of any of [1] to [15].
[17] A cell preparation comprising the cell of [16].
[18] An NKT cell activator comprising the cell of [16].
[19] An agent for treating or preventing cancer or an infectious disease, comprising the cell of [16].
[20] A method for activating an NKT cell in a test subject, comprising administering the cell of [16] or the cell preparation of [17] to the test subject.
[21] The method of [20], wherein the test subject is affected with cancer or an infectious disease, or has a history of having cancer or an infectious disease.
[22] A method for treating or preventing cancer or an infectious disease in a test subject, comprising administering the cell of [16] or the cell preparation of [17] to the test subject.
[23] The cell of [16] for use in activating an NKT cell.
[24] The cell of [16] for use in treating or preventing cancer or an infectious disease.
[25] The cell preparation of [17] for use in activating an NKT cell.
[26] The cell preparation of [17] for use in treating or preventing cancer or an infectious disease.
[27] Use of the cell of [16] in producing a medicament for activating an NKT cell.
[28] Use of the cell of [16] in producing a medicament for treating or preventing cancer or an infectious disease.

Effect of the Invention

According to the present invention, an NKT cell ligand-pulsed cell having a strong NKT cell activating capacity is expected to be produced in a relatively short period. The NKT cell ligand-pulsed cell obtained by the method of the present invention strongly induces proliferation of NKT cells, IFN-γ production and cytotoxic activity of NKT cells. It may therefore be useful as a cell preparation for the treatment or prophylaxis of diseases such as cancer, infectious disease and the like; or metastasis or recurrence of cancer.

BRIEF DESCRIPTION OF THE DRAWINGS

FIG. 1 shows comparison of the surface antigen expression patterns of human peripheral blood CD14 positive cells (before pulsing with RK-163), "RK-163-pulsed human CD14 positive cell" obtained by culturing CD14 positive cells for 2 days in the presence of NKT cell ligands RK-163 and GM-CSF, and "RK-163-pulsed human dendritic cell" cultured for 6 days in the presence of NKT cell ligands RK-163 and GM-CSF and IL-4. Shading indicates negative control antibody. In addition, a surface antigen expression pattern of "RK-163-pulsed human Elu-CD14 positive cell" obtained by culturing CD14 positive cells, obtained from the apheresis fluid of human peripheral blood by an elutriation method using an automatic cell separator, for 2 days in the presence of NKT cell ligands RK-163 and GM-CSF is also shown. The "RK-163-pulsed human Elu-CD14 positive cell" showed the same results (CD14 positive, CD1d positive, CD40 positive) as the RK-163-pulsed CD14 positive cells obtained by other separation method.

FIG. 2 shows comparison results of IFN-γ production inducing potency (NKT cell activation action) of "RK-163-pulsed human CD14 positive cells, "RK-163-pulsed human CD14 negative cell" prepared from CD14 negative cells, and "RK-163-pulsed human dendritic cell".

FIG. 10-1 shows surface antigen expression pattern of human CD14 positive cell line THP-1 cells.

FIG. 10-2 shows surface antigen expression pattern of human CD14 positive cell line U937 cells.

FIG. 10-3 shows surface antigen expression pattern of human iPS-CD14 positive cell line.

FIG. 12 shows correlation between RK-163 pulsing time in producing RK-163-pulsed human CD14 positive cell line and IFN-γ production inducing effect on human NKT cell line.

FIG. 14B shows an antitumor effect induced by RK-163-pulsed human CD14 positive cell line (THP-1 cell, U937 cell).

FIG. 19B shows induction of memory T cells by RK-163-pulsed human CD14 positive cell line.

DESCRIPTION OF EMBODIMENTS

Figure 3:
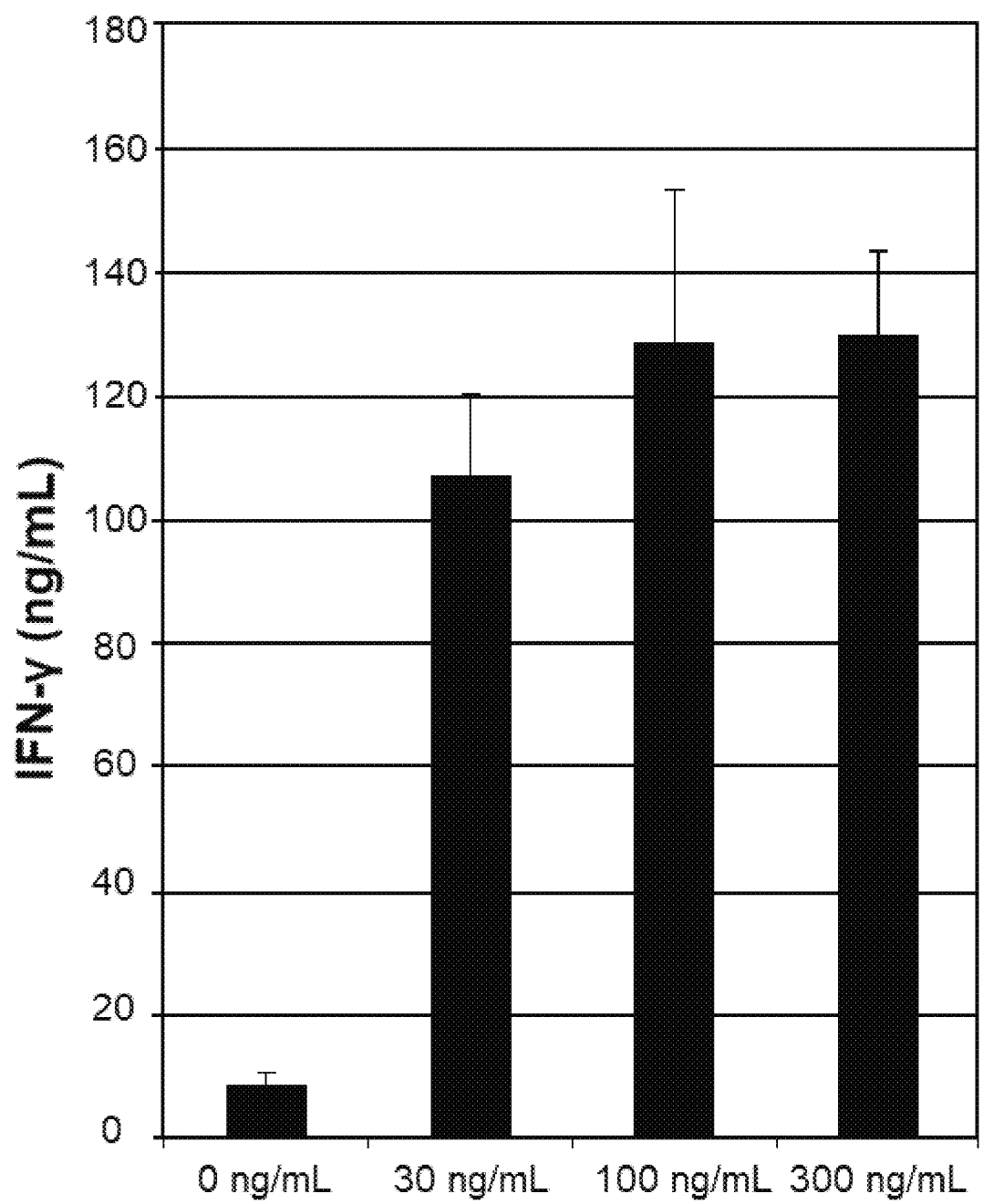
FIG. 3 shows IFN-γ production inducing potency (NKT cell activation action) of "RK-163-pulsed human CD14 positive cell" prepared by culturing human peripheral blood CD14 positive cells at various RK-163 pulse concentrations.

<NKT Cell Ligand-Pulsed Cells>:

The present invention provides an NKT cell ligand-pulsed cell. The NKT cell ligand-pulsed cell of the present invention, namely, NKT cell ligand-pulsed CD14 positive cell and NKT cell ligand-pulsed CD14 positive cell line, activates NKT cells and has an activity to induce proliferation of NKT cells, IFN-γ production, adjuvant action, long-term immune memory induction and/or cytotoxic activity against tumor cells.

The "NKT cell ligand pulse" means that an NKT cell ligand taken up into a cell is presented on a cell membrane by a Cd1d protein. The definitions of the "NKT cell", "NKT cell ligand", "CD14 positive cell" and "CD14 positive cell line" are described in detail below. The NKT cell ligand is not particularly limited as long as it is a compound that binds to CD1d, is specifically recognized, when presented on the CD1d molecule, by a T cell receptor (NKT cell receptor) on NKT cell and peculiar to the NKT cell, and can specifically activate NKT cells. For example, NKT cell ligand is a glycolipid having the aforementioned activity, preferably α-GalCer or an analog thereof and, in view of the fact that it strongly induces IFN-γ production of NKT cells, the compounds described in III or VI are preferable, particularly, RCAI-85, RCAI-137 or RK-163 (RCAI-124) is preferable, from among the NKT cell ligands described below. A most preferable NKT cell ligand is RK-163 (RCAI-124).

The NKT cell ligand-pulsed cell of the present invention may be a mammalian cell. Examples of the mammal include rodents such as mouse, rat, hamster, guinea pig and the like, experiment animals such as rabbit and the like; domestic animals such as swine, bovine, goat, horse, sheep, mink and the like; pets such as dog, cat and the like; and primates such as human, monkey, *Macaca* mulatta, marmoset, orangutan, chimpanzee and the like. A preferable mammal is primate, more preferably human.

When a treatment is performed using the NKT cell ligand-pulsed cell of the present invention, the NKT cell ligand-pulsed cell of the present invention is preferably allogeneic to the test subject (patient). For example, an NKT cell ligand-pulsed human cell is administered to human. The NKT cell ligand-pulsed cell of the present invention is an autologous cell (genetically syngeneic) or a heterologous cell (genetically allogeneic).

The NKT cell ligand-pulsed cell of the present invention is preferably CD14 positive. The proportion of the CD14 positive cells in the NKT cell ligand-pulsed cells of the present invention is, for example, not less than 50%, preferably not less than 60%, not less than 70%, not less than 80% or not less than 90%.

The NKT cell ligand-pulsed cell of the present invention is preferably CD1d positive. The proportion of the CD1d positive cells in the NKT cell ligand-pulsed cells of the present invention is, for example, not less than 50%, preferably not less than 60%, not less than 70%, not less than 80% or not less than 90%.

The NKT cell ligand-pulsed cell of the present invention is preferably CD40 positive. The proportion of the CD40 positive cells in the NKT cell ligand-pulsed cells of the present invention is, for example, not less than 50%, preferably not less than 60%, not less than 70%, not less than 80% or not less than 90%.

In a preferable embodiment, the NKT cell ligand-pulsed cell of the present invention is CD14 positive CD1d positive CD40 positive. The proportion of the CD14 positive CD1d positive CD40 positive cells in the NKT cell ligand-pulsed cells of the present invention is, for example, not less than 50%, preferably not less than 60%, not less than 70%, not less than 80% or not less than 90%.

In one embodiment, the NKT cell ligand-pulsed cell of the present invention is a monocyte or a cell line established from a monocyte. The cell line can be established by any known method selected by those of ordinary skill in the art. CD14 is a well-known monocyte marker.

The NKT cell ligand-pulsed cell of the present invention is not a dendritic cell. Therefore, expression of a dendritic cell marker in the NKT cell ligand-pulsed cell of the present invention is limitative or the NKT cell ligand-pulsed cell of the present invention does not express dendritic cell marker. The proportion of the CD209 (dendritic cell marker) positive cells in the NKT cell ligand-pulsed cells of the present invention is, for example, not more than 40%, preferably not more than 30%, not more than 20%, not more than 10%, not more than 5% or not more than 1% (e.g., 0%). The dendritic cell is generally CD14 negative.

The NKT cell ligand-pulsed cell of the present invention is isolated. "Isolation" means that an operation to remove factors other than the desired cell and component has been done and the naturally occurring state is absent. The purity of the "isolated NKT cell ligand-pulsed cell" (percentage of the number of NKT cell ligand-pulsed cells to the total number of cells) is generally not less than 70%, preferably not less than 80%, not less than 90%, not less than 95%, not less than 98%, not less than 99% or not less than 99.5%, most preferably 100%.

The NKT cell ligand-pulsed cell of the present invention can be produced, for example, by the method described below.

<Production Method of NKT Cell Ligand-Pulsed Cells>
(Production Method 1)

The present invention provides a production method of an NKT cell ligand-pulsed cell, including a step of culturing isolated CD14 positive cells in a medium containing an NKT cell ligand and GM-CSF and substantially free of IL-4 (Production method 1 of the present invention).

CD14 is a glycosyl-phosphatidylinositol (GPI)-bound single chain membrane glycoprotein having a molecular weight of 53-55 kDa and is known as a marker cell surface antigen of monocyte. The cell corresponding to the CD14 positive cell is preferably differentiated from a hematopoietic stem cell in all mammals and is a progenitor cell before differentiation into macrophage or dendritic cell, more preferably monocyte.

In the present specification, when the phenotype of a cell is expressed by the presence or absence of the expression of a marker molecule (antigen), it is indicated by the presence or absence of specific binding by an antibody to the marker molecule unless otherwise specified. Determination of the phenotype of a cell by the presence or absence of the expression of a marker molecule is generally performed by flow cytometric analysis using a specific antibody against the marker molecule or the like. "Positive" expression of the marker molecule means that the marker molecule is expressed on the cell surface and that specific binding by an antibody to the marker molecule can be confirmed.

The CD14 positive cell used in Production method 1 may be derived from a mammal. The mammal is not particularly limited as long as the NKT cell ligand-pulsed cell can be produced by Production method 1. Examples of the mammal include rodents such as mouse, rat, hamster, guinea pig and the like, experiment animals such as rabbit and the like; domestic animals such as swine, bovine, goat, horse, sheep, mink and the like; pets such as dog, cat and the like; and primates such as human, monkey, *Macaca* mulatta, marmoset, orangutan, chimpanzee and the like. A preferable mammal is primate, more preferably human.

In the present specification, the nomenclature of CD14 follows that of human CD14.

There may be cases where mammals other than human do not have an antigen gene corresponding to human CD14. In the present invention, regardless of the presence or absence of the expression of CD14, monocytes of such mammals are treated as cells corresponding to the "CD14 positive cells".

When a treatment is performed using the cell obtained by Production method 1, the CD14 positive cell (e.g., monocyte) used in Production method 1 is preferably allogeneic to the subject. The CD14 positive cell (e.g., monocyte) to be used in the present invention is an autologous cell (genetically syngeneic) or a heterologous cell (genetically allogeneic).

The CD14 positive cell (e.g., monocyte) to be used in Production method 1 is isolated from a tissue containing CD14 positive cells. Examples of the tissue include, but are not limited to, peripheral blood, cord blood, bone marrow, spleen, thymus, lymph node, liver, tumor tissue, and the like. The CD14 positive cell (e.g., monocyte) to be used in Production method 1 is preferably isolated from peripheral blood or cord blood. Isolated CD14 positive cell may be a CD14 positive cell line established as a cell line from CD14 positive cells isolated from a tissue containing CD14 positive cells. Establishment of a cell line can be performed according to a known method freely selected by those of ordinary skill in the art. Furthermore, the isolated CD14-positive cell may be a CD14-positive cell established again by differentiation induction after reprogramming any cell. Examples of the method for reprogramming any cell include, but are not limited to, the methods described in U.S. Pat. Nos. 8,048,999, 8,058,065, 8,129,187, 8,278,104, 8,791,248, 9,145,547. As a method for obtaining a CD14 positive cell from a reprogrammed cell, for example, Grigoriadis et al., Blood. 2010 Apr. 8; 115(14):2769-76 and Stem Cells. 2016 December; 34(12):2852-2860 may be referred to. The method is not limited thereto since those of ordinary skill in the art can freely optimize the method.

The CD14 positive cell (e.g., monocyte) to be used in Production method 1 is isolated. "Isolation" means that an operation to remove factors other than the desired cell and component has been done and the naturally occurring state is absent. The purity of the "isolated CD14 positive cell" (percentage of the number of CD14 positive cells to the total number of cells) is generally not less than 70%, preferably not less than 80%, not less than 90%, not less than 95%, not less than 98%, not less than 99% or not less than 99.5%, most preferably 100%. Other kinds of cells are similarly defined.

CD14 positive cell (e.g., monocyte) can be isolated from the aforementioned tissue containing CD14 positive cells (e.g., monocytes) by using an antibody that specifically binds to CD14 and according to a method such as antibody-bound magnetic bead, cell sorter, panning and the like. In addition, the CD14 positive cell (e.g., monocyte) can be isolated from apheresis fluid of human peripheral blood by an elutriation method using an automatic cell separator.

For example, first, a mononuclear cell fraction is prepared from peripheral blood, cord blood and the like. The mononuclear cell fraction is prepared by, for example, density gradient centrifugation using Ficoll-Paque PLUS (GE Healthcare Japan), apheresis fluid and the like. Next, the mononuclear cell fraction is stained with an antibody that specifically binds to CD14 and is labeled with a fluorescent dye, magnetic beads or the like, and CD14 positive cells (e.g., monocytes) are isolated using a cell sorter, a magnetic column and the like. CD14 positive cells (e.g., monocytes) may be isolated from the mononuclear cell fraction by a simple panning method including attaching the CD14 positive cells to a petri dish. Also, it is possible to use a CD14 positive cell (e.g., monocyte) concentrated fraction obtained from an apheresis fluid of human peripheral blood by an elutriation method using an automatic cell separator (manufactured by TERUMO etc.).

An antibody that specifically binds to other marker (e.g., MHC Class I-like molecule (CD1d etc.), CD11b, CD15, CD86 etc.) of monocytes and macrophages may also be used in place of the antibody that specifically binds to CD14.

At the start of culture, the proportion of the CD1d positive cells in the isolated CD14 positive cells to be used in Production method 1 is generally not less than 70%, preferably not less than 80%, not less than 90%, not less than 95%, not less than 98%, not less than 99% or not less than 99.5%, most preferably 100%.

Then, the isolated CD14 positive cells are cultured in a medium containing an NKT cell ligand and GM-CSF and substantially free of IL-4. Preferably, primary culture of CD14 positive cells isolated from the aforementioned biological tissue is performed in a medium containing an NKT cell ligand and GM-CSF and substantially free of IL-4.

NKT cell is a lymphocyte expressing two antigen receptors of NK receptor-specific T cell receptor (invariant TCR) and NK receptor. Different from general T cells, the repertoire of T cell receptor on the NKT cell is very limited. For example, a chain of T cell receptor on the mouse NKT cell (sometimes to be referred to as Vα14 NKT cell) is encoded by invariant Vα14 and Jα18 gene segments (Proc Natl Acad Sci USA, 83, p. 8708-8712, 1986; Proc Natl Acad Sci USA, 88, p. 7518-7522, 1991; J Exp Med, 180, p. 1097-1106, 1994), and a chain of T cell receptor on the human NKT cell is encoded by invariant Vα24 highly homologous to mouse Vα14 and Jα18 gene segments. NKT cells recognize "NKT cell ligand" presented on the CD1d molecule by the T cell receptor on the cell (this is called NKT cell receptor).

NKT cell ligand is a compound that is specifically recognized, when presented on the CD1d molecule, by a T cell receptor (NKT cell receptor) on NKT cell and peculiar to the NKT cell, and can specifically activate NKT cells. The NKT cell ligand usable in the present invention is, for example, a glycolipid having the aforementioned activity, preferably α-GalCer or an analog thereof. For example, the following compound can be mentioned.

I. A Compound of the Formula (I) or a Salt or Solvate Thereof.

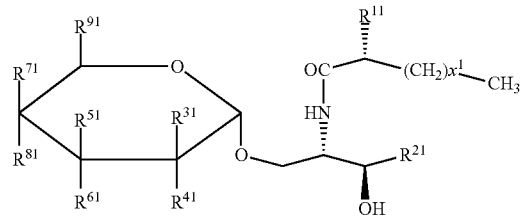
(I)

(in the above-mentioned formula, $R^{11}$ is H or OH, $X^1$ is an integer of any of 7-27, $R^{21}$ is a substituent selected from the group consisting of the following (a)-(e) ($Y^1$ is an integer of any of 5-17), (a) —CH$_2$(CH$_2$)$_{Y1}$CH$_3$, (b) —CH(OH)(CH$_2$)$_{Y1}$CH$_3$, (c) —CH(OH)(CH$_2$)$_{Y1}$CH(CH$_3$)$_2$, (d) —CH=CH(CH$_2$)$_{Y1}$CH$_3$, (e) —CH(OH)(CH$_2$)$_{Y1}$CH(CH$_3$)CH$_2$CH$_3$, and $R^{31}$-$R^{91}$ are substituents defined by the following i) or ii): i) $R^{31}$, $R^{61}$, and when $R^{81}$ is H, $R^{41}$ is H, OH, NH$_2$, NHCOCH$_3$, or a substituent selected from the group consisting of the following groups (A)-(D):

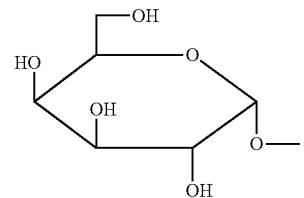
(A)

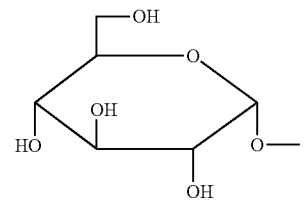
(B)

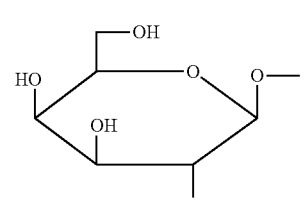
(C)

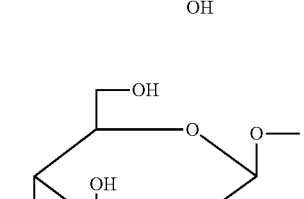
(D)

and $R^{51}$ is OH or a substituent selected from the following groups (E) and (F):

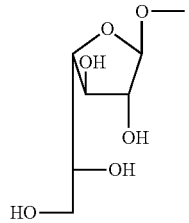
(E)

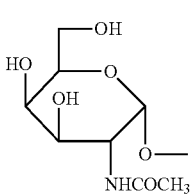
(F)

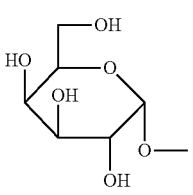
(A)

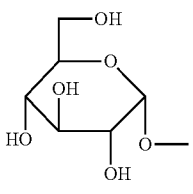
(B)

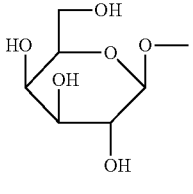
(C)

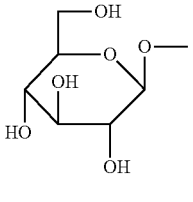
(D)

$R^{71}$ is OH or a substituent selected from the group consisting of the following groups (A)-(D):

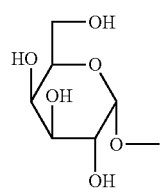
(A)

-continued (B) 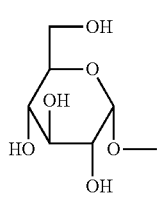

(C) 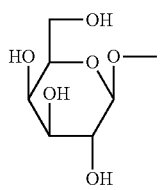

(D) 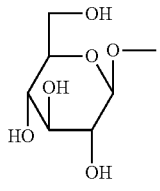

$R^{91}$ is H, $CH_3$, $CH_2OH$ or a substituent selected from the group consisting of the following groups (A')-(D'):

(A') 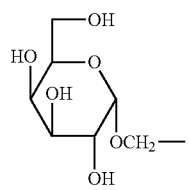

(B') 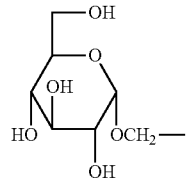

(C') 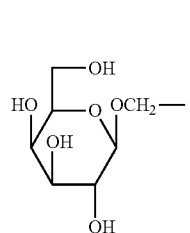

(D') 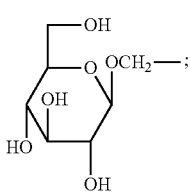

ii) When $R^{31}$, $R^{61}$ and $R^{71}$ are each H, $R^{41}$ is H, OH, $NH_2$, $NHCOCH_3$ or a substituent selected from the group consisting of the following groups (A)-(D):

(A) 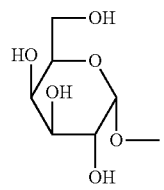

(B) 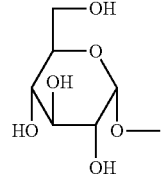

(C) 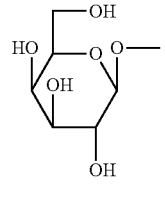

(D) 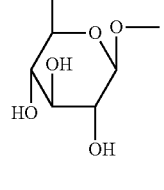

$R^{51}$ is OH or a substituent selected from the group consisting of the following groups (E) and (F):

(E) 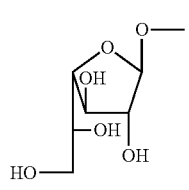

(F) 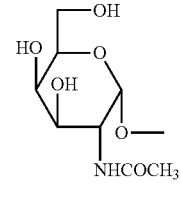

$R^{81}$ is OH or a substituent selected from the group consisting of the following groups (A)-(D):

(A) 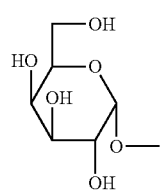

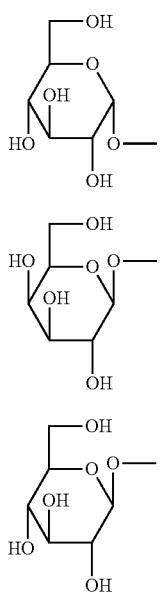

(B)

(C)

(D)

R$^{91}$ is H, CH$_3$, CH$_2$OH or a substituent selected from the group consisting of the following groups (A')-(D'):

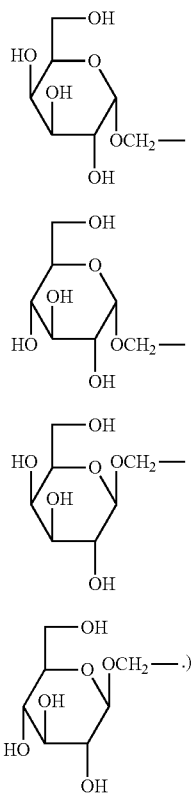

(A')

(B')

(C')

(D')

Among these, (2S,3S,4R)-1-O-(α-D-galactopyranosyl)-2-hexacosanoylamino-1,3,4-octadecanetriol (to be also referred to as α-galactosylceramide, α-GalCer, in the present specification) is preferable. The structural formula of α-GalCer is shown in the following formula (a):

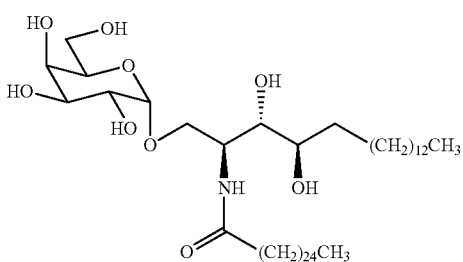

The compound of the formula (I) can be produced by the methods described in WO 94/09020, WO 94/02168, WO 94/24142, WO 98/44928, Science, 278, p. 1626-1629, 1997 and the like.

II. Compound Represented by the Formula (II) or a Salt Thereof.

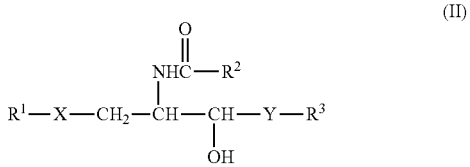

wherein R$^1$ is a α-carbasugar residue, R$^2$ and R$^3$ are each independently a substituted or unsubstituted hydrocarbon group having 1-28 carbon atoms, X is an oxygen atom, a sulfur atom, —CH$_2$— or —NH—, and Y is —CH$_2$—, —CH(OH)— or —CH=CH—.

Particularly, the following compounds are preferable.

[1] (2S,3S,4R)-1-(5a-carba-α-D-galactopyranosyloxy)-2-(hexacosanoylamino)-3,4-octadecanediol
[2] (2S,3S,4R)-1-(5a-carba-α-D-galactopyranosylthio)-2-(hexacosanoylamino)-3,4-octadecanediol
[3] (2S,3S,4R)-1-(5a-carba-α-D-glucopyranosyloxy)-2-(hexacosanoylamino)-3,4-octadecanediol
[4] (2S,3S,4R)-1-(5a-carba-α-D-glucopyranosylthio)-2-(hexacosanoylamino)-3,4-octadecanediol
[5] (2S,3S,4R)-1-(5a-carba-α-D-fucopyranosyloxy)-2-(hexacosanoylamino)-3,4-octadecanediol The compound of the formula (II) or a salt thereof can be produced by the methods described in WO 2008/102888, U.S. Pat. No. 8,299,223 and the like.

III. Compound Represented by the Formula (III) or a Salt Thereof.

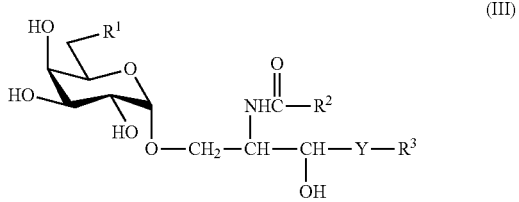

wherein R$^1$ is a hydrogen atom, an alkyl group having 1-7 carbon atoms, an alkoxy group having 1-6 carbon atoms or a halogen atom, R$^2$ and R$^3$ are each independently a substituted or unsubstituted hydrocarbon group having 1-28 carbon atoms, and Y is —CH$_2$—, —CH(OH)— or —CH=CH—, provided that when R$^1$ is a hydrogen atom, R$^2$ is a substituted or unsubstituted hydrocarbon group having 24-28 carbon atoms.

Particularly, the following compounds are preferable.
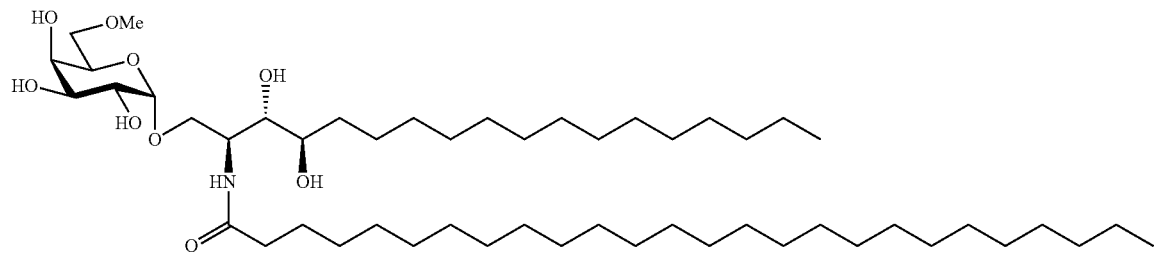
RCAI-61
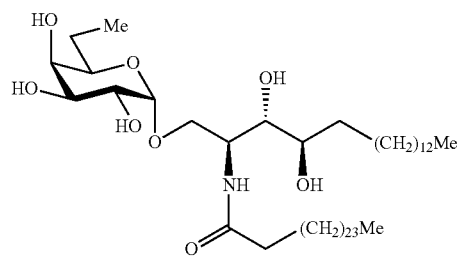
RCAI-64
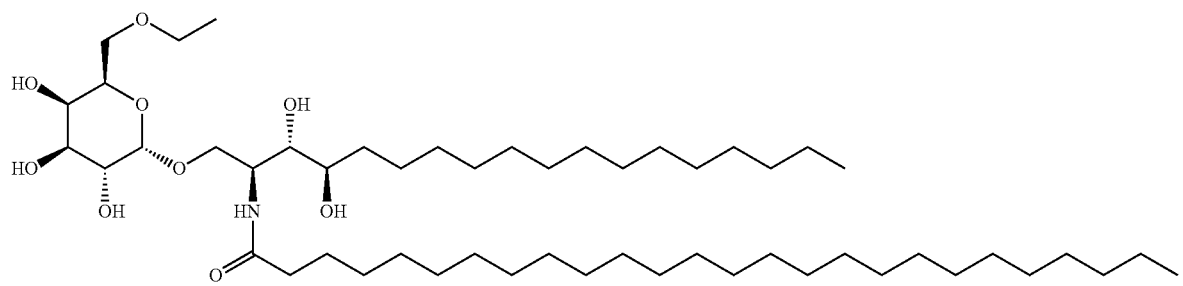
RCAI-85
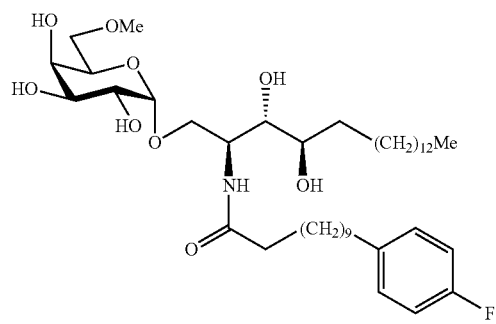
RCAI-165

The compound of the formula (III) or a salt thereof can be produced by the methods described in WO 2009/119692, U.S. Pat. No. 8,551,959 and the like.

IV. Compound Represented by the Formula (IV) or a Salt Thereof.

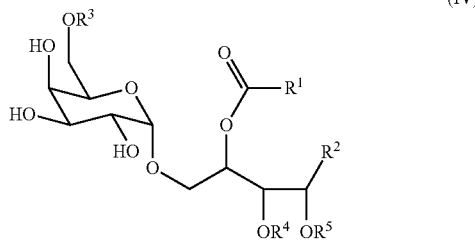

(IV)

wherein $R^1$ is a hydrocarbon group having 1-30 carbon atoms, $R^2$ is a hydrocarbon group having 1-20 carbon atoms, $R^3$ is a hydrogen atom or a hydrocarbon group having 1-5 carbon atoms, $R^4$ and $R^5$ are the same or different and each is a hydrogen atom or a hydrocarbon group having 1-5 carbon atoms, or $R^4$ and $R^5$ are joined to form a divalent hydrocarbon group having 1-5 carbon atoms, which optionally forms a ring structure with the adjacent ethylenedioxy.

The compound of the formula (IV) or a salt thereof can be produced by the methods described in WO 2010/030012, U.S. Pat. No. 8,580,751 and the like.

V. Compound Represented by the Formula (V) or a Salt Thereof.

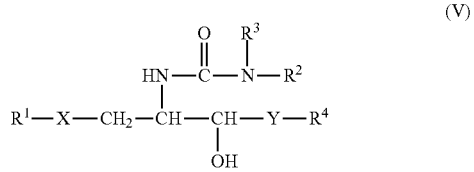

(V)

wherein $R^1$ is an aldopyranose residue in which the 6-position hydroxyl group is optionally alkylated, $R^2$ is a hydrocarbon group having 1-26 carbon atoms and optionally having substituent(s), $R^3$ is a hydrogen atom or a hydrocarbon group having 1-26 carbon atoms and optionally having substituent(s), $R^4$ is a hydrocarbon group having 1-21 carbon atoms and optionally having substituent(s), X is an oxygen atom or —$CH_2$—, and Y is —$CH_2$—, —CH(OH)— or —CH═CH—.

Particularly, the following compounds or salts thereof are preferable.

[1] (2S,3S,4R)-1-(α-D-galactopyranosyloxy)-2-(tetracosanoylureido)-3,4-octadecanediol
[2] (2S,3S,4R)-1-(α-D-galactopyranosyloxy)-2-(hexadecanylureido)-3,4-octadecanediol
[3] (2S,3S,4R)-1-(6-O-methyl-α-D-galactopyranosyloxy)-2-(tetracosanoylureido)-3,4-octadecanediol The compound of the formula (V) or a salt thereof can be produced by the methods described in WO 2011/552842, U.S. Pat. No. 8,853,173 and the like.

VI. Compound Represented by the Formula (VI), or a Salt Thereof.

A compound represented by

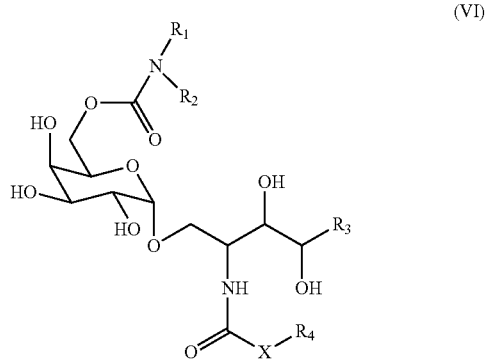

(VI)

wherein
X is an alkylene group or —NH—;
$R_1$ and $R_2$ are the same or different and each is a hydrogen atom, an alkyl group, a hydroxyl group, an alkoxy group, or an aryl group optionally having a substituent, $R_1$ and $R_2$ optionally form, together with the adjacent nitrogen atom, a 5- or 6-membered ring;
$R_3$ is a hydrocarbon group having 1-20 carbon atoms;
$R_4$ is a hydrocarbon group having 1-30 carbon atoms, or a salt thereof.

Particularly, the following compound is preferable.

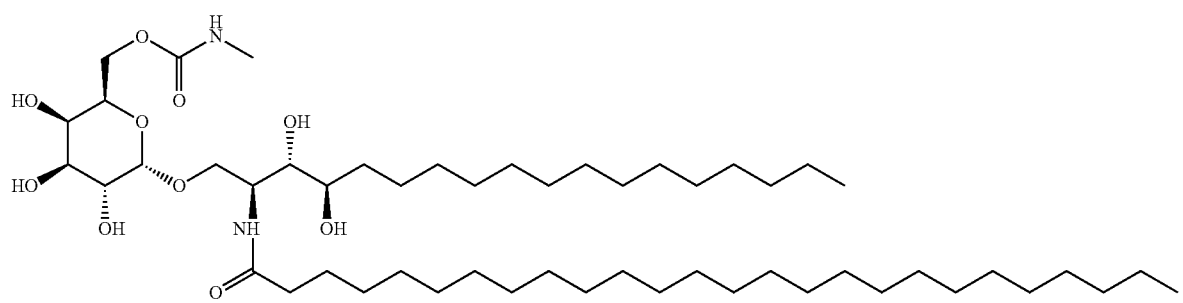

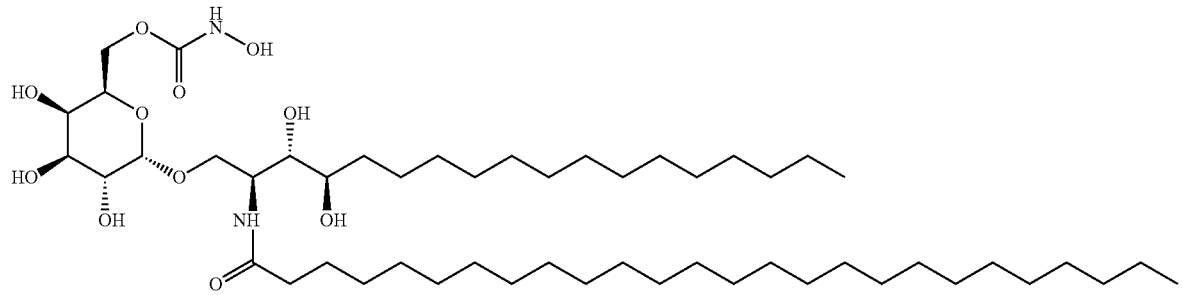

RCAI-137

The compound of the formula (VI) or a salt thereof can be produced by the methods described in WO 2013/162016 A1, US 2015/152128 A1 and the like.

To strongly induce IFN-γ production of NKT cells, the compound described in the above-mentioned III or VI is preferable among the NKT cell ligands described above, and particularly,
RCAI-85
RCAI-137
RK-163 (RCAI-124)
are preferable.

The NKT cell ligand to be used in Production method 1 is most preferably RK-163 (RCAI-124).

The concentration of the NKT cell ligand in the medium used for culturing the CD14 positive cells (e.g., monocytes) is not particularly limited as long as the NKT cell ligand-pulsed cells obtained by Production method 1 can activate the NKT cells. It is generally not less than 1 ng/mL, preferably not less than 10 ng/mL, more preferably not less than 30 ng/mL. Theoretically, the upper limit of the concentration of the NKT cell ligand in the medium is the solubility thereof. Even if the concentration is set unnecessarily high, the action of the NKT cell ligand-pulsed cells to activate NKT cells reaches a plateau. From the aspect of culture costs, it is generally not more than 10000 ng/mL, preferably not more than 1000 ng/mL, more preferably not more than 300 ng/mL. Therefore, the concentration range of the NKT cell ligand to be added to the medium is generally 1-10000 ng/mL, preferably 10-1000 ng/mL, more preferably 30-300 ng/mL.

GM-CSF is added to the medium to be used for culturing CD14 positive cells (e.g., monocytes). The concentration of GM-CSF in the medium is not particularly limited as long as expression of CD40 in the NKT cell ligand-pulsed cells obtained after culturing is induced. It is generally not less than 6.7 ng/mL, preferably not less than 33.3 ng/mL, more preferably not less than 53.3 ng/mL. Theoretically, the upper limit of the concentration of GM-CSF in the medium is the solubility thereof. Even if the concentration is set unnecessarily high, the action thereof reaches a plateau. From the aspect of culture costs, it is generally not more than 666.7 ng/mL, preferably not more than 133.3 ng/mL, more preferably not more than 66.7 ng/mL. Therefore, the concentration of GM-CSF in the medium is generally 6.7-666.7 ng/mL, preferably 33.3-133.3 ng/mL, more preferably 53.3-66.6 ng/mL. When the GM-CSF concentration is expressed by biological activity (IU) thereof, the following conversion formula is applied to the above-mentioned concentration.
GM-CSF 1 mg=$1.5 \times 10^7$ IU Importantly, the medium to be used for culturing CD14 positive cells (e.g., monocytes) is substantially free of IL-4.

When isolated CD14 positive cells (e.g., monocytes) are cultured in a medium containing GM-CSF and IL-4, immature dendritic cells can be induced. In the dendritic cells, expression of CD1d was scarcely recognized, and the ability to activate NKT cells by presenting NKT cell ligands to the NKT cells is low. In contrast, in Production method 1, cells with high ability to activate NKT cells while maintaining CD1d expression can be obtained by culturing isolated CD14 positive cells (e.g., monocytes) in a medium containing GM-CSF and substantially free of IL-4. Being "substantially free of IL-4" means that the concentration of IL-4 in the medium is lower than the concentration at which isolated CD14 positive cells (e.g., monocytes) are induced into immature dendritic cells. The concentration of IL-4 in the medium to be used for culturing CD14 positive cells is generally less than 0.01 ng/mL, preferably less than 0.001 ng/mL, more preferably less than 0.0001 ng/mL (e.g., 0 ng/mL). Therefore, in a preferable embodiment, exogenous IL-4 is not added to the culture in culturing isolated CD14 positive cells (e.g., monocytes).

The medium to be used for culturing CD14 positive cells (e.g., monocytes) is preferably substantially free of Flt-3L. While Flt-3L can promote differentiation of CD14 positive cells into dendritic cells, differentiation into dendritic cells is not desirable in Production method 1. In addition, addition of Flt-3L may decrease cell survival rate, viable cell number, and cell recovery rate after culturing the CD14 positive cells. Being "substantially free of Flt-3L" means that the concentration of Flt-3L in the medium is lower than the concentration at which isolated CD14 positive cells are induced into immature dendritic cells. In one embodiment, the concentration of Flt-3L in the medium to be used for culturing CD14 positive cells is generally less than 0.01 ng/mL, preferably less than 0.001 ng/mL, more preferably less than 0.0001 ng/mL (e.g., 0 ng/mL). Therefore, in a preferable embodiment, exogenous Flt-3L is not added to the culture in culturing isolated CD14 positive cells (e.g., monocytes).

The medium to be used for culturing CD14 positive cells (e.g., monocytes) is preferably substantially free of SCF. While involvement of SCF in the differentiation into dendritic cells has been reported, differentiation into dendritic cells is not desirable in Production method 1. In addition, addition of SCF may decrease cell survival rate, viable cell number, and cell recovery rate after culturing the CD14 positive cells. Being "substantially free of SCF" means that the concentration of Flt-3L in the medium is lower than the concentration promoting differentiation into dendritic cell. In one embodiment, the concentration of SCF in the medium to be used for culturing CD14 positive cells is generally less than 0.01 ng/mL, preferably less than 0.001 ng/mL, more preferably less than 0.0001 ng/mL (e.g., 0 ng/mL). Therefore, in a preferable embodiment, exogenous SCF is not added to the culture in culturing isolated CD14 positive cells (e.g., monocytes).

The medium to be used for culturing CD14 positive cells (e.g., monocytes) is preferably substantially free of IL-2. IL-2 activates T cells contaminating the culture to induce production of IL-4 and this IL-4 may promote differentiation of CD14 positive cells into dendritic cells. Being "substantially free of IL-2" means that the concentration of IL-2 in the medium is lower than the concentration activating T cells. In one embodiment, the concentration of IL-2 in the medium to be used for culturing CD14 positive cells is generally less than 0.01 ng/mL, preferably less than 0.001 ng/mL, more preferably less than 0.0001 ng/mL (e.g., 0 ng/mL). Therefore, in a preferable embodiment, exogenous IL-2 is not added to the culture in culturing isolated CD14 positive cells (e.g., monocytes).

The medium to be used for culturing CD14 positive cells (e.g., monocytes) may contain, In addition to GM-CSF, one or plural kinds of cytokines (interleukin, chemokine, interferon, hematopoietic factor, cell growth factor, cytotoxic factor, adipokine, neurotrophic factor etc.) other than those mentioned above, as long as NKT cell ligand-pulsed cells that efficiently activate NKT cells can be produced by Production method 1.

In one embodiment, the medium to be used for culturing CD14 positive cells (e.g., monocytes) is substantially free of cytokines (interleukin, chemokine, interferon, hematopoietic factor, cell growth factor, cytotoxic factor, adipokine, neurotrophic factor etc.) other than GM-CSF. In this embodiment, the concentration of each cytokine other than GM-CSF in the medium is, for example, less than 0.01 ng/mL, preferably less than 0.001 ng/mL, more preferably less than 0.0001 ng/mL (e.g., 0 ng/mL). In a preferable embodiment, exogenous cytokine other than GM-CSF is not added to the culture in culturing isolated CD14 positive cells (e.g., monocytes).

The proteinaceous factor to be added to the culture medium in Production method 1 may be derived from the same animal species as the CD14 positive cells (for example, monocytes) to be cultured, or may be derived from a different animal species. Preferably, it is derived from the same animal species. For example, when human CD14 positive cells (e.g., human monocytes) are cultured, human-derived proteinaceous factor (e.g., human GM-CSF etc.) is added. "Human-derived" proteinaceous factor means that the amino acid sequence of the factor is identical to the amino acid sequence of the factor naturally expressed in human.

As the basal medium of the medium to be used for culturing CD14 positive cells (e.g., monocytes), those known per se can be used and is not particularly limited as long as NKT cell ligand-pulsed cells can be produced by Production method 1. For example, RPMI-1640, DMEM, EMEM, α-MEM, F-12, F-10, M-199, HAM and the like can be mentioned. A medium modified for culturing lymphocytes and the like (e.g., AIM-V) may also be used, and a mixture of the above-mentioned basal media may be used.

The medium may contain additives known per se. The additive is not particularly limited as long as NKT cell ligand-pulsed cells can be produced by Production method 1. For example, organic acid (e.g., sodium pyruvate etc.), amino acid (e.g., non-essential amino acid, L-glutamine etc.), reducing agent (e.g., 2-mercaptoethanol etc.), buffering agent (e.g., HEPES etc.), antibiotic (e.g., streptomycin, penicillin, gentamicin etc.) and the like can be mentioned. Each additive is preferably contained in a concentration range known per se.

The medium may or may not contain serum. The serum is not particularly limited as long as it is derived from a mammal and NKT cell ligand-pulsed cells can be produced by Production method 1. It is preferably a serum derived from the above-mentioned mammal (e.g., fetal bovine serum, human serum etc.). Autologous serum of a test subject from which the CD14 positive cells (e.g., monocytes) to be cultured were collected may be used. An alternative additive (e.g., Knockout Serum Replacement (KSR) (manufactured by Invitrogen) etc.) for serum may also be used in place of the serum. While the concentration of the serum is not particularly limited as long as NKT cell ligand-pulsed cells can be produced by Production method 1, it is generally 0.1-30 (v/v) %.

From the aspect of avoiding contamination of chemically-undefined components, the medium used for culturing CD14 positive cells (e.g., monocytes) may preferably be a serum-free medium. The serum-free medium means a medium that does not contain unadjusted or unpurified serum, and a medium containing components derived from purified blood and components (e.g., growth factor) derived from animal tissue corresponds to the serum-free medium.

Isolated CD14 positive cells (e.g., monocytes) can be cultures by, for example, centrifuging CD14 positive cells (e.g., monocytes) isolated from the aforementioned biological sample to recover cells, removing the supernatant medium, suspending the cells in the aforementioned medium containing NKT cell ligand and GM-CSF and substantially free of IL-4, seeding the cells in a culture dish and culturing them for a given time. The isolated CD14 positive cells (e.g., monocytes) may be suspended in a medium not containing NKT cell ligand and/or GM-CSF and substantially free of IL-4, seeded in a culture dish, and NKT cell ligand and/or GM-CSF may be added to the medium to a given concentration. culture can be appropriately scaled-up by controlling the culture dish and the like according to the desired object.

The seeding density of CD14 positive cells (e.g., monocytes) at the start of culture is not particularly limited as long as NKT cell ligand-pulsed cells can be produced by Production method 1. Since comparatively high survival rate, recovery rate, and the surviving cell number are expected to be achieved, it is generally $0.42\times10^6$-$3.42\times10^6$ (cells/cm$^2$), preferably, $1.68\times10^6$-$3.42\times10^6$ (cells/cm$^2$). The area of the denominator indicates the bottom area of the culture container.

The culture period (i.e., pulse time by NKT cell ligand) of the isolated CD14 positive cells (e.g., monocytes) in a medium containing NKT cell ligand is not particularly limited as long as NKT cell ligand-pulsed cells can be produced by Production method 1. From the aspect of certainly presenting NKT cell ligand and enhancing the ability to activate NKT cells, it is generally not less than 16 hr, preferably 16-72 hr, more preferably 20-72 hr.

As other culture conditions, those generally used in the lymphocyte culture technique can be used. For example, the culture temperature is generally about 30-40° C., preferably about 37° C. The $CO_2$ concentration is generally about 1-10%, preferably about 5%. The humidity is generally about 70-100%, preferably about 95-100%.

By such culturing operation, the NKT cell ligand is taken up into CD14 positive cells (e.g., monocytes) and presented on the cell membrane by CD1d protein, whereby NKT cell ligand-pulsed cells can be obtained.

The NKT cell ligand-pulsed cells obtained in Production method 1 activate NKT cells and have the activity of inducing proliferation of NKT cells, production of IFN-γ and/or cytotoxic activity against tumor cells.

That the NKT cell ligand-pulsed cell was obtained can be confirmed by coculturing the cells after culturing and isolated NKT cells and evaluating IFN-γ production. By coculturing the NKT cell ligand-pulsed cells and isolated NKT cells, NKT cells are activated and production of IFN-γ is induced.

The NKT cell ligand-pulsed cell obtained by Production method 1 is preferably CD14 positive. The proportion of the CD14 positive cells in the NKT cell ligand-pulsed cells obtained by Production method 1 is, for example, not less than 50%, preferably not less than 60%, not less than 70%, not less than 80% or not less than 90%.

The NKT cell ligand-pulsed cell obtained by Production method 1 is preferably CD1d positive. The proportion of the CD1d positive cells in the cell population obtained by the above-mentioned culturing is, for example, not less than 50%, preferably not less than 60%, not less than 70%, not less than 80% or not less than 90%.

The NKT cell ligand-pulsed cell obtained by Production method 1 is preferably CD40 positive. The proportion of the CD40 positive cells in the cell population obtained by the above-mentioned culturing is, for example, not less than 50%, preferably not less than 60%, not less than 70%, not less than 80% or not less than 90%.

In a preferable embodiment, the NKT cell ligand-pulsed cell obtained by Production method 1 is CD14 positive CD1d positive CD40 positive. The proportion of the CD14 positive CD1d positive CD40 positive cells in the cell population obtained by above-mentioned culturing is, for example, not less than 50%, preferably, not less than 60%, not less than 70%, not less than 80% or not less than 90%. By culturing isolated CD14 positive cells (e.g., monocytes) in a medium containing an NKT cell ligand and GM-CSF and substantially free of IL-4, expression of CD40, which is important for activation of NKT cells, is induced while maintaining expression of CD1d, and cells with high ability to activate NKT cells are expected to be obtained.

Production method 1 can include a washing step to remove excess NKT cell ligand released in the medium after culturing isolated CD14 positive cells (e.g., monocytes) in a medium containing an NKT cell ligand and GM-CSF and substantially free of IL-4 and recovering the NKT cell ligand-pulsed cells. For washing, an appropriate medium, saline, phosphate buffered saline, Ringer's solution and the like can be used.

(Production Method 2)

The present invention provides a production method of an NKT cell ligand-pulsed CD14 positive cell line, including a step of culturing CD14 positive cell line, obtained by establishing (immortalizing) CD14 positive cells such as monocyte and the like, in a medium containing an NKT cell ligand and substantially free of GM-CSF and IL-4 (Production method 2 of the present invention).

The CD14 positive cell line may be a cell line established from CD14 positive cells such as monocyte and the like. The CD14 positive cell line can be prepared by, for example, culturing in a medium substantially free of GM-CSF and IL-4. The CD14 positive cell line can be prepared according to the above-mentioned Production method 1 except that the medium used for the culturing may not contain NKT ligand.

In addition, a CD14 positive cell line that fulfills the object can also be obtained by selecting a cell line satisfying the CD14 positive CD1d positive expression pattern from among the cell lines established from monocytes and the like. Examples of such cell line include THP-1 and U937.

It is also possible to use a CD14 positive cell line differentiated and established from a reprogrammed cell (pluripotent stem cell) such as an iPS cell and the like. As a method for obtaining a CD14 positive cell line from a reprogrammed cell, for example, Grigoriadis et al., Blood. 2010 Apr. 8; 115(14):2769-76 and Stem Cells. 2016 December; 34(12):2852-2860 may be referred to. The method is not limited thereto since those of ordinary skill in the art can freely optimize the method.

The CD14 positive cell line to be subjected to Production method 2 is preferably isolated.

The CD14 positive cell line to be subjected to Production method 2 is preferably CD14 positive. At the start of culture, the proportion of the CD1d positive cells in the isolated CD14 positive cell line to be used in Production method 2 is generally not less than 70%, preferably not less than 80%, not less than 90%, not less than 95%, not less than 98%, not less than 99% or not less than 99.5%, most preferably 100%.

CD14 positive cell line can be cultured in a medium containing NKT cell ligand according to the above-mentioned Production method 1 except that the medium used for culturing is substantially free of GM-CSF.

The concentration of GM-CSF in the medium to be used for culturing CD14 positive cell line is generally less than 0.01 ng/mL, preferably less than 0.001 ng/mL, more preferably less than 0.0001 ng/mL (e.g., 0 ng/mL). Therefore, in a preferable embodiment, exogenous GM-CSF is not added to the culture in culturing CD14 positive cell line.

The culture period (i.e., pulse time by NKT cell ligand) of the isolated CD14 positive cell line in a medium containing NKT cell ligand is not particularly limited as long as NKT cell ligand-pulsed CD14 positive cell line can be produced by Production method 2. It is generally not less than 2 hr, preferably 2-72 hr. Production method 2 requires a short time compared to Production method 1 and, for example, a pulse time of about 2 hr can afford the ability to activate NKT cells. Therefore, the pulse time in Production method 2 may be, for example, not more than 32 hr, not more than 24 hr, not more than 8 hr, not more than 7 hr, not more than 4 hr.

The NKT cell ligand-pulsed CD14 positive cell line obtained in Production method 2 activates NKT cells and has the activity of inducing proliferation of NKT cells, production of IFN-γ and/or cytotoxic activity against tumor cells.

The NKT cell ligand-pulsed CD14 positive cell line obtained in Production method 2 is preferably CD14 positive. The proportion of the CD14 positive cells in the cell population obtained by the above-mentioned culturing is, for example, not less than 50%, preferably not less than 60%, not less than 70%, not less than 80% or not less than 90%.

The NKT cell ligand-pulsed CD14 positive cell line obtained by Production method 2 is preferably CD1d positive. The proportion of the CD1d positive cells in the cell population obtained by the above-mentioned culturing is, for example, not less than 50%, preferably not less than 60%, not less than 70%, not less than 80% or not less than 90%.

The NKT cell ligand-pulsed CD14 positive cell line obtained by Production method 2 is preferably CD40 positive. The proportion of the CD40 positive cells in the cell population obtained by the above-mentioned culturing is, for example, not less than 50%, preferably not less than 60%, not less than 70%, not less than 80% or not less than 90%.

In a preferable embodiment, the NKT cell ligand-pulsed CD14 positive cell line obtained by Production method 2 is CD14 positive CD1d positive CD40 positive. The proportion of the CD14 positive CD1d positive CD40 positive cells in the cell population obtained by the above-mentioned culture is, for example, not less than 50%, preferably not less than 60%, not less than 70%, not less than 80% or not less than 90%. By culturing the CD14 positive CD1d positive cell line in a medium containing NKT cell ligand and substantially free of GM-CSF and IL-4, the NKT cell ligand is rapidly presented on CD1d, CD40 enhances expression and a cell having high ability to activate NKT cells is expected to be obtained.

Production method 2 can include a washing step to remove excess NKT cell ligand released in the medium after culturing CD14 positive cell line in a medium containing an NKT cell ligand and substantially free of GM-CSF and IL-4 and recovering the NKT cell ligand-pulsed CD14 positive cell line. For washing, an appropriate medium, saline, phosphate buffered saline, Ringer's solution and the like can be used.

<Cell Preparation Containing NKT Cell Ligand-Pulsed CD14 Positive Cell or NKT Cell Ligand-Pulsed CD14 Positive Cell Line>

The present invention also provides a cell preparation containing the above-mentioned NKT cell ligand-pulsed CD14 positive cell or NKT cell ligand-pulsed CD14 positive cell line of the present invention. The NKT cell ligand-pulsed CD14 positive cell and NKT cell ligand-pulsed CD14 positive cell line can be respectively obtained by the above-mentioned Production method 1 and Production method 2 of the present invention. The NKT cell ligand-pulsed CD14 positive cell or NKT cell ligand-pulsed CD14 positive cell line contained in the cell preparation of the present invention may be in a state in which each cell is suspended, the cells are coagulated to form a cell aggregate, or non-adherent cells and aggregates are mixed. The NKT cell ligand-pulsed CD14 positive cell or NKT cell ligand-pulsed CD14 positive cell line is generally suspended in a pharmaceutically acceptable dilution carrier, for example, saline, buffer and the like. The NKT cell ligand-pulsed CD14 positive cell or NKT cell ligand-pulsed CD14 positive cell line can be formulated as a cell preparation by adding a protein such as albumin and the like, and additive such as a pharmacologically active ingredient and the like as necessary, and optionally placing the mixture in a container such as vial, bag, syringe and the like. The number of NKT cell ligand-pulsed cells per 1 vial or 1 dose can be adjusted to, for example, $1 \times 10^5$-$1 \times 10^9$ cells. Alternatively, the NKT cell ligand-pulsed CD14 positive cells or NKT cell ligand-pulsed CD14 positive cell lines may be concentrated and used to give a cell preparation. The dilution carrier, protein and additive can be appropriately selected to be compatible with the cell population contained in the cell preparation. It is also possible to further add a protector such as DMSO and the like and freeze the mixture to give a cell preparation.

The cell preparation of the present invention can be used as an NKT cell activator or a prophylactic or therapeutic agent for diseases (described in detail below) for which prophylactic or therapeutic effects are expected directly or indirectly by proliferation of NKT cells (increase in NKT cell count), IFN-γ production and/or cytotoxic activity, each induced by activation of NKT cells.

<Prophylactic or Treatment Method of Diseases for which Prophylactic or Therapeutic Effects are Expected Directly or Indirectly by Proliferation of NKT Cells (Increase in NKT Cell Count), IFN-γ Production and/or Cytotoxic Activity, Each Induced by Activation of NKT Cells, the Method Including Administration of NKT Cell Ligand-Pulsed CD14 Positive Cell or NKT Cell Ligand-Pulsed CD14 Positive Cell Line>

According to the present invention, NKT cells in the test subjects can be activated by administering the above-mentioned NKT cell ligand-pulsed CD14 positive cell or NKT cell ligand-pulsed CD14 positive cell line of the present invention, or a cell preparation containing the NKT cell ligand-pulsed CD14 positive cell or NKT cell ligand-pulsed CD14 positive cell line to the test subjects. Particularly, in the present invention, proliferation of NKT cells (increase in NKT cell count), IFN-γ production, adjuvant action, long-term immune memory, and/or cytotoxic activity can be induced by activating NKT cells in the test subjects. Thus, the diseases for which prophylactic or therapeutic effects are expected directly or indirectly by proliferation of NKT cells (increase in NKT cell count), IFN-γ production, adjuvant action, long-term immune memory and/or cytotoxic activity, each induced by activation of NKT cells in the test subjects, are expected to be prevented or treated by administering the above-mentioned NKT cell ligand-pulsed CD14 positive cell or NKT cell ligand-pulsed CD14 positive cell line of the present invention, or a cell preparation containing the NKT cell ligand-pulsed CD14 positive cell or NKT cell ligand-pulsed CD14 positive cell line to the test subjects.

In the present specification, the "test subject" refers to a subject to be treated by the method of the present invention. For example, mammals such as human, mouse, rat, rabbit, dog, cat, bovine, horse, monkey, swine and the like can be mentioned. It is preferably human.

Examples of the diseases for which prophylactic or therapeutic effects are expected directly or indirectly by proliferation of NKT cells (increase in NKT cell count), IFN-γ production, adjuvant action, long-term immune memory and/or cytotoxic activity, each induced by activation of NKT cells include various carcinomas (e.g., breast cancer, colorectal cancer, lung cancer, prostate cancer, esophagus cancer, gastric cancer, liver cancer, biliary cancer, spleen cancer, renal cancer, urinary bladder cancer, uterine cancer, testis cancer, thyroid cancer, pancreatic cancer, brain tumor, ovarian cancer, skin cancer, blood tumor (e.g., adult T cell leukemia, chronic myeloid leukemia, malignant lymphoma and the like) and the like); various infectious diseases, for example, viral disease (e.g., viral hepatitis due to hepatitis B virus, hepatitis C virus, hepatitis D virus, herpes, acquired immunodeficiency syndrome (AIDS), epidemic influenza and the like), bacterium infectious disease (e.g., medicament resistance tuberculosis, atypical mycobacterial infection and the like), mycosis (e.g., *candida* infection and the like) and the like. The test subject is suitably a mammal (e.g., human) affected with cancer or having a past medical history of cancer, or a mammal (e.g., human) affected with an infectious disease or having a past medical history of infectious disease. The cell preparation of the present invention may also be applicable to the treatment or prophylaxis of infectious disease, cancer metastasis or recurrence.

NKT cells can activate various immune cells (e.g., cytotoxic T cells, NK cells, etc.) that act directly on cancer cells and pathogen-infected cells in the body. Thus, the cell preparation of the present invention may be applicable to the treatment or prophylaxis of infectious diseases irrespective of the kind of cancer or pathogens.

The administration method is not limited as long as it can make the cell preparation of the present invention reach NKT cells existing in or around the affected part. For example, intravenous administration, intraarterial administration, intramucosal administration, administration into lymph node, administration into affected part tissue and the like can be mentioned. Specifically, the cell preparation can be delivered directly to the disease site of the patient through an injection needle. In addition, the cell preparation can also be administered into vein or artery through a catheter.

The number of cell populations to be administered in one time is not particularly limited as long as it is a number sufficient to activate NKT cells existing in or around the affected part and to prevent or treat a target disease. For example, it is $1\times10^4$-$1\times10^9$ cells/body weight kg, preferably $1\times10^5$-$1\times10^7$ cells/body weight kg, more preferably $1\times10^5$-$1\times10^6$ cells/body weight kg. In addition, the concentration of the cells in the cell preparation is generally $1\times10^4$-$1\times10^7$ cells/mL, preferably $1\times10^5$-$5\times10^6$ cells/mL, more preferably $3\times10^5$-$3\times10^6$ cells/mL. The administration may be performed plural times depending on the condition of the test subject, the severity of the disease and the like.

The NKT cell ligand-pulsed CD14 positive cell or NKT cell ligand-pulsed CD14 positive cell line to be administered to a test subjects can be prepared from autologous CD14 positive cells (e.g., monocytes) (genetically syngeneic), or heterologous (genetically allogeneic) CD14 positive cells (e.g., monocytes) or CD14 positive cell line (including CD14 positive cell line differentiation-induced and established from reprogrammed cells such as iPS cell and the like). It is preferable to administer NKT cell ligand-pulsed CD14 positive cells prepared from the test subject's own CD14 positive cells (e.g., monocytes) to the test subject. It is also preferable to administer to a test subject predicted to have compatibility with heterologous NKT cell ligand-pulsed CD14 positive cell or NKT cell ligand-pulsed CD14 positive cell line.

The contents disclosed in any publication cited in the present specification, including patents and patent applications, are hereby incorporated in their entireties by reference, to the extent that they have been disclosed herein.

The present invention is explained in more detail in the following by referring to Examples. The present invention is not restricted by the following Examples and the like.

EXAMPLES

Example 1

1. Material and Method
1) Starting Materials: Separation and Purification of CD14 Positive Cell (Monocyte) from Cord Blood and Healthy Individual Peripheral Blood
(1) Separation and Purification from Human Peripheral Blood Using Anti-CD14 Antibody of CD14 Positive Cell (Monocyte)

A mononuclear cell layer was separated from the peripheral blood (300 mL) of a volunteer healthy individual by using Ficoll-Paque PLUS (GE healthcare Japan, Code No. 17144002) (number of recovered cells: $9.7\times10^8$), and CD14 positive cells were separated and purified using anti-CD14 antibody-bound microbeads (Miltenyi Biotech, Order no. 130-050-201) (number of recovered cells: $10.7\times10^8$, recovery rate: 10.5%, CD14 positive rate: 99.2%, survival rate: 98.0%). A part of the cells were subjected to differentiation culture of dendritic cells. The cell fractions not separated using the anti-CD14 antibody-bound microbeads were recovered as CD14 negative cells.

(2) Separation and Purification of CD14 Positive Cell (Monocyte) from Human Peripheral Blood Apheresis Fluid Using Cell Separator A monocyte cell fraction was separated from the peripheral blood apheresis fluid (99 mL) of a volunteer healthy individual by using a cell separator (manufactured by TERUMO: Elutra) (number of recovered cells: $1.1\times10^9$), and human CD14 positive cells (human Elu-CD14 positive cells) were separated (recovered total cell number: $1.1\times10^9$, monocyte recovery rate: 49.1%, CD14 positive rate: 75.1%, survival rate: 98.3%). In the separation and purification by this method, the recovery rate was dramatically improved as compared to the separation and purification using the CD14 antibody. As a result, many CD14 positive cells could be obtained.

(3) Separation and Purification of CD14 Positive Cell (Monocyte) from Human Cord Blood CD14 positive cells (monocytes) were separated and purified from human cord blood, from which most of erythrocytes had been removed using HES (hydroethyl starch), and frozen with a freezing agent containing dextran (RIKEN BioResource center, Tsukuba) (containing total leukocytes) using anti-CD14 antibody-bound microbeads (Miltenyi Biotech, Order no. 130-050-201) (number of recovered cells: $10.7\times10^8$, recovery rate: 10.5%, CD14 positive rate: 99.2%, survival rate: 98.0%). A part of the cells were subjected to differentiation culture of dendritic cells. The cell fractions not separated using the anti-CD14 antibody-bound microbeads were recovered as CD14 negative cells.

2) Production of Antigen Presenting Cell for Activation of NKT Cell Using CD14 Positive Cell (Monocyte)
(1) Production of "RK-163-Pulsed Human CD14 Positive Cell" and "RK-163-Pulsed Human Elu-CD14 Positive Cell" by Culturing for 2 Days with GM-CSF Addition Human monocytes (CD14 positive cells) immediately after separation using anti-CD14 antibody and monocytes (CD14 positive cells) (human Elu-CD14 positive cells) obtained from apheresis fluid of human peripheral blood by an elutriation method were respectively resuspended in AIM-V medium added with cytokine [53.3 ng/mL Recombinant Human GM-CSF (Miltenyi Biotec) alone] at a cell density of $3\times10^6$/mL, and seeded in a 24-well culture plate (Falcon) at 1 mL/well. Simultaneously, RK-163 (bulk powder was dissolved in PBS added with DMSO and 0.5% Tween 20) was added to a final concentration 100 ng/mL, and the cells were cultured at 37° C., 5% $CO_2$ for 48 hr to give "RK-163-pulsed human CD14 positive cell" and "RK-163-pulsed human Elu-CD14 positive cell". The survival rate, recovery rate, and NKT activation action (IFN-γ production, cell number increase, cytotoxic activity) were measured as follows.

(2) Differentiation Culture of CD14 Positive Cell (Monocyte) into Dendritic Cell (DC) and Production of "RK-163-Pulsed Human Dendritic Cell"

For comparison of a novel technique with the conventional method, the human CD14 positive cells (monocytes) obtained in 1) were suspended in AIM-V (Gibco, code no. 0870112-DK) medium at a cell concentration of $1\times10^6$/mL and seeded in a 6-well culture plate (Falcon) at 5 mL/well. Recombinant Human GM-CSF 53.3 ng/mL and IL-4 34.7 ng/mL (both Miltenyi Biotech) were added and the mixture was cultured at 37° C., 5% $CO_2$ for 6 days to induce differentiation into dendritic cells. Thereafter, RK-163 (bulk powder was dissolved in PBS added with DMSO and 0.5% Tween 20) was added to a final concentration 100 ng/mL, and the cells were cultured at 37° C., 5% $CO_2$ for 48 hr to give "RK-163-pulsed human dendritic cell".

3) Analysis Method (1) Calculation Method of Viable Cell Number and Survival Rate After staining with 0.4% Trypan Blue (Bio-Rad), unstained viable cells and blue-stained dead cells were measured twice with TC20™ Automated Cell Counter (Bio-Rad). The average thereof was calculated and the viable cell number and survival rate were calculated.

(2) Fluorescence Activated Cell Sorting (FACS) Analysis

Phycoerythrin-labeled anti-human antibody against each of the following antigens [CD14 (clone HCD14, Biolegend), CD11c (clone 3.9, Biolegend), CD11b (clone ICRF44, BD Biosciences), CD45 (clone HI30, Biolegend), HLA-DR (clone L243, Biolegend), CD1d (clone 51.1, Biolegend), CD40 (clone 5C3, Biolegend), CD95(Fas) (clone DX2, Biolegend), CD80 (clone 2D10, Biolegend), CD86 (clone IT2.2, Biolegend), and CD209 (clone DC-SIGN, Miltenyi Biotech)] was added to the cells, and static reaction was performed under shading for 30 min at 4° C. After centrifugation and washing, the cells were suspended in 0.5% human serum albumin-added PBS, and the purity of CD14 positive cells and expression of various surface antigens were examined by a flow cytometer (FACSCantoII, BD Biosciences).

(3) Measurement of NKT Cell Activating Action (IFN-γ Production)

For preparation of the cells obtained by culturing human CD14 positive cells (monocytes) immediately after separation using anti-CD14 antibody and human CD14 negative cells or human Elu-CD14 positive cells (monocytes) for 2 days with GM-CSF and NKT cell ligand RK-163 (respectively called "RK-163-pulsed human CD14 positive cell", "RK-163-pulsed human CD14 negative cell", "RK-163-pulsed human Elu-CD14 positive cell"), and the dendritic cells induced to differentiate in 2)-(2) by culturing for 6 days with addition of GM-CSF and IL-4 (called "RK-163-pulsed human dendritic cell"), RK-163 (bulk powder was dissolved in PBS added with DMSO and 0.5% Tween 20) was added to each cell to a final concentration of 100 ng/mL, and the cells were cultured at 37° C., 5% $CO_2$ for 48 hr to produce "RK-163-pulsed cells". After culturing, the recovered cells were centrifugation washed twice, and the number of viable cells after Trypan Blue staining was calculated by TC20™ Automated Cell Counter. RK-163-pulsed cells and human NKT cell line were respectively suspended in 10% fetal calf serum (Sigma, Lot No. 114K525)-added RMPI-1640 (Invitrogen) to $1\times10^6$/mL, each cell suspension was seeded at a cell concentration of $1\times10^5$/0.1 mL/well in a 96-well round-bottomed culture plate, and the cells were cultured at 37° C., 5% $CO_2$ for 48 hr. After culturing, 200 μL of supernatant was recovered, and the produced and secreted IFN-γ was measured using a commercially available ELISA kit (BD Biosciences).

This research is based on RIKEN "Ethical Provisions Regarding Human-Targeted Studies" and obtained an approval from the Institute's Ethics Review Committee prior to the start of the research. This research was conducted in compliance with the provisions of the preamble and "Ethics Guidelines on Medical Research for Human" (Ministry of Education, Culture, Sports, Science and Technology, Ministry of Health, Labor and Welfare).

2. Results and Discussion (1) Surface Antigen Expression Patterns of Human Peripheral Blood "CD14 Positive Cell (Monocyte)", "RK-163-Pulsed Human CD14 Positive Cell" "RK-163-Pulsed Human Elu-CD14 Positive Cell" and "RK-163-Pulsed Human Dendritic Cell"

In CD14 positive cells (monocytes) immediately after isolation from human peripheral blood, expression of CD1d and CD14 antigen was extremely high, and characteristics (CD14 negative, CD209 positive) of the dendritic cell were scarcely observed.

On the other hand, in the "RK-163-pulsed human CD14 positive cell" cultured for 2 days with NKT cell ligand RK-163 in the presence of GM-CSF, expression of CD40 which activates NKT cells and induces INF-γ production was rapidly enhanced, but the characteristics of dendritic cell (CD14 negative, CD209 positive) were not found. The "RK-163-pulsed human CD14 positive cell" and "RK-163-pulsed human Elu-CD14 positive cell" still expressed CD14 and CD1d. Being CD14 positive cells, they were confirmed to be cells different from dendritic cell.

Figures 1, 10:
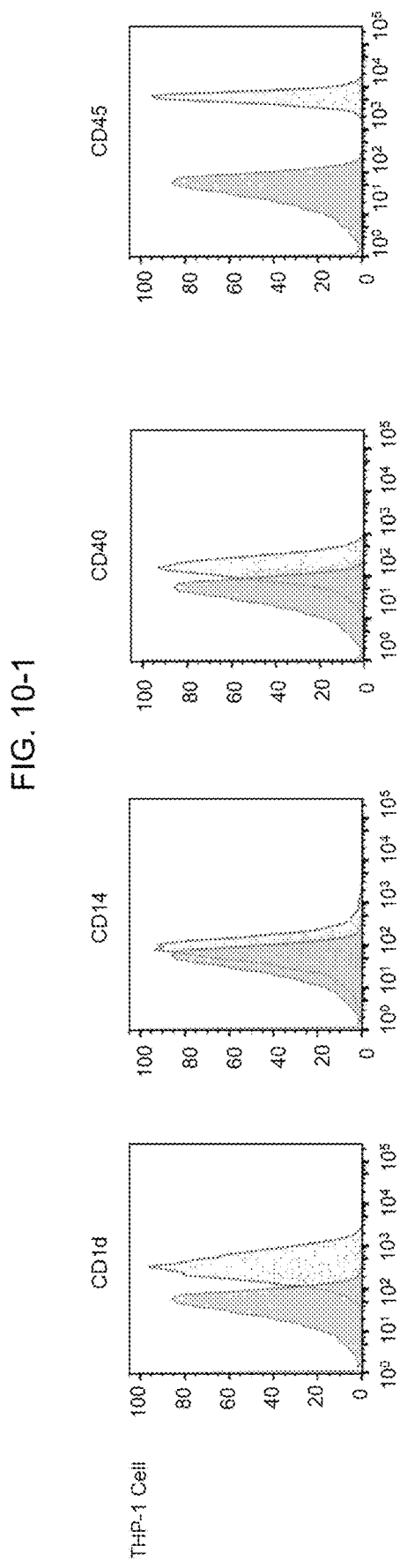

In the "RK-163-pulsed human dendritic cell" obtained by culturing CD14 positive cells (monocytes) for 6 days in the presence of GM-CSF+IL-4, high expression of CD40 was found. However, expression of CD14 antigen was hardly observed and the expression of CD1d also decreased markedly (FIG. 1). CD1d binds to NKT ligand (RK-163) and is an essential molecule for activation of NKT cells, along with the expression of CD40. Thus, the "RK-163-pulsed CD14 positive cell" was considered to be optimal for NKT cell activation since it shows high expression of the both. On the other hand, the decrease in the expression of CD1d in the "RK-163-pulsed human dendritic cell" suggests that it may be the cause of the lowered activation of NKT cells even though the expression of CD40 molecule essential for NKT cell activation is observed.

Figures 2, 10:
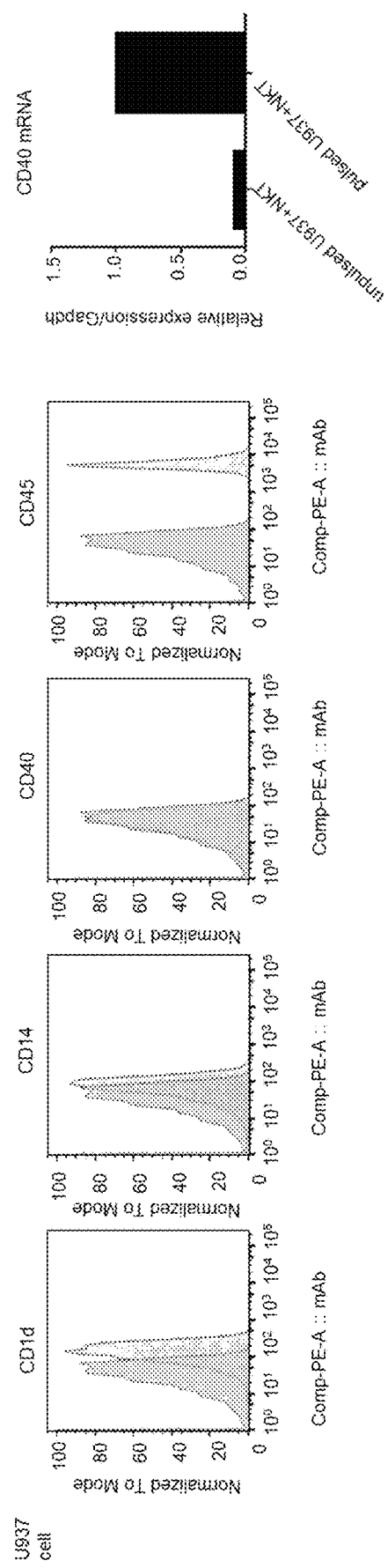
Figures 3, 10:
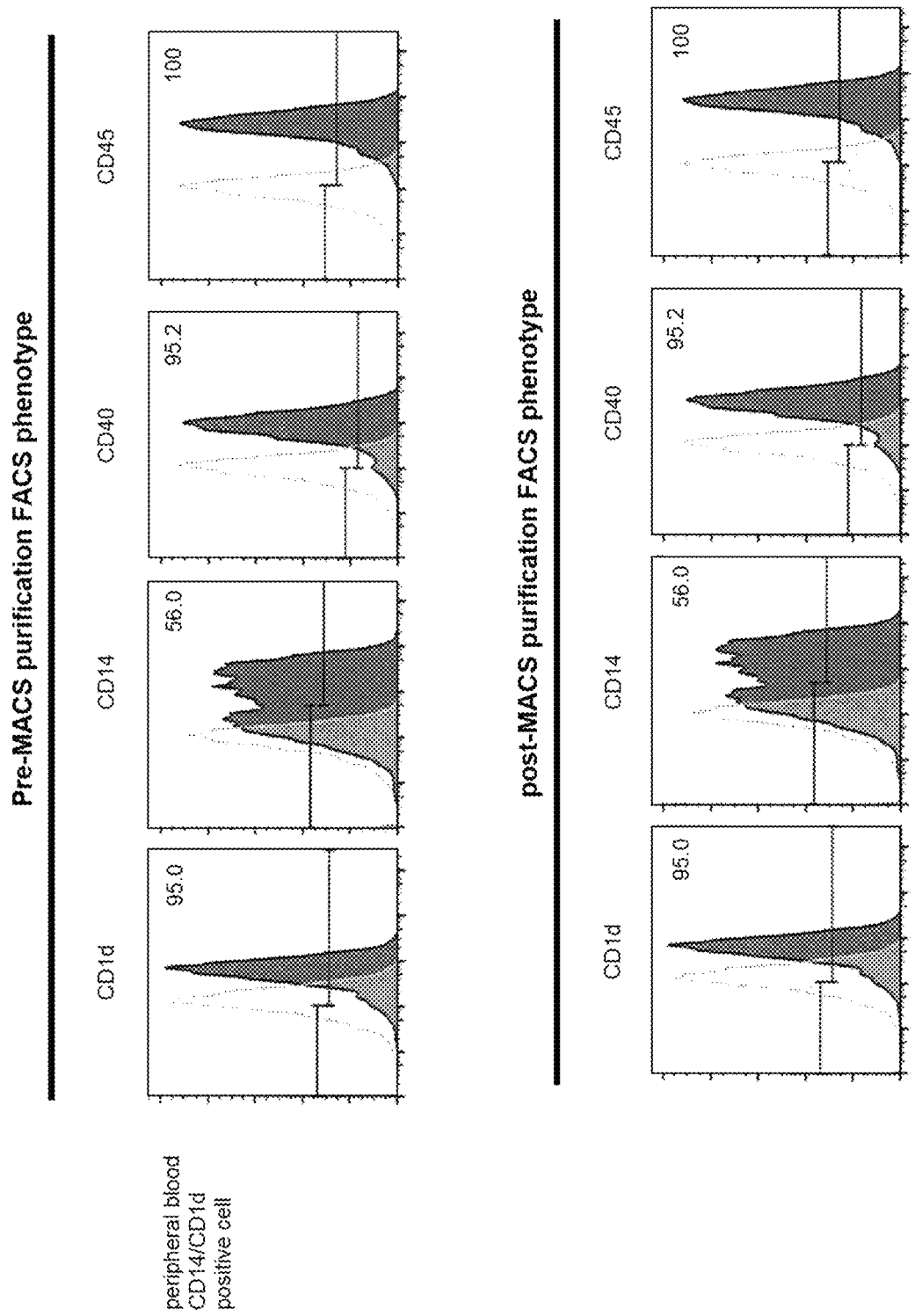

(2) Comparison of IFN-γ Production Induction Potency (NKT Cell Activating Action) of "RK-163-Pulsed Human CD14 Positive Cell", "RK-163-Pulsed Human CD14 Negative Cell", "RK-163-Pulsed Human Dendritic Cell" Prepared from Human Peripheral Blood CD14 Positive Cell (Monocyte) or CD14 Negative Cell The IFN-γ production was examined when human NKT cell line was co-cultured with "RK-163-pulsed human CD14 positive cell" to find that it was about 3 times higher than when co-cultured with "RK-163-pulsed human dendritic cell". The NKT cell activation ability of "RK-163-pulsed human CD14 negative cell" obtained by pulsing "CD14 negative cell", immediately after separation by CD14 antibody-bound microbeads, with ligand (i.e., IFN-γ production from NKT cells) was low (FIG. 2). The results reveal that the "RK-163-pulsed human CD14 positive cell" shows an extremely high NKT cell activating action as compared to "RK-163-pulsed human dendritic cell" and "RK-163-pulsed human CD14 negative cell".

(3) CD14 positive cells (monocytes) isolated from human peripheral blood were cultured in a GM-CSF-containing medium for 48 hr in the presence of various concentrations of RK-163 and the NKT cell activating effect (IFN-γ production induction) of the obtained RK-163-pulsed CD14 positive cells was evaluated. As a result, it was shown that RK-163 pulsing at a concentration of 30 ng/mL-300 ng/mL affords RK-163-pulsed CD14 positive cells having an NKT cell activating effect (FIG. 3).

(4) Influence of RK-163 Pulse Time on IFN-γ Production Induction Potency (NKT Cell Activating Action) in Preparing "RK-163-Pulsed Human CD14 Positive Cell"

Figure 4:
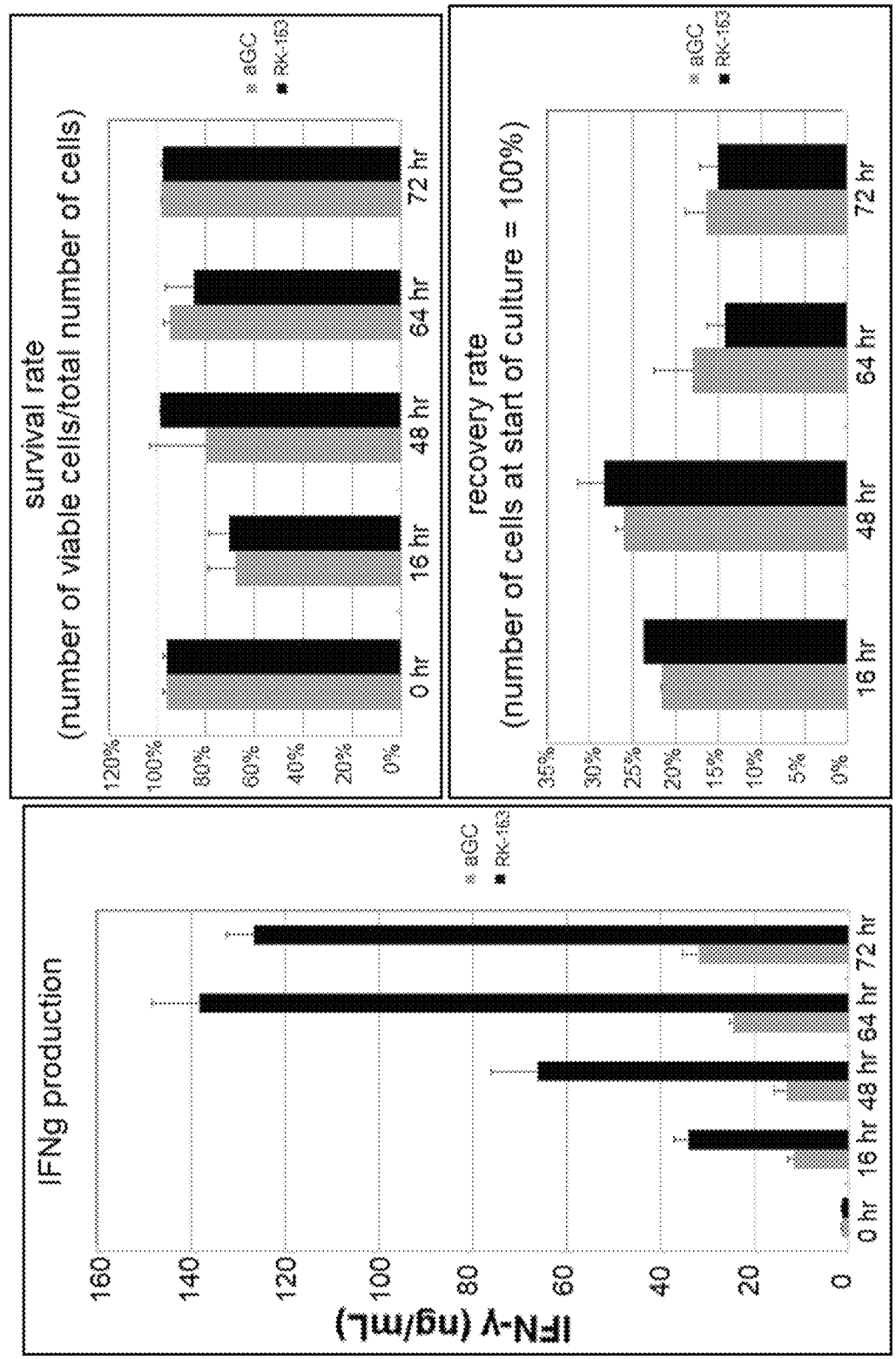
FIG. 4 shows IFN-γ production inducing potency relative to NKT cells (NKT cell activation action), recovery rate and survival rate of "RK-163-pulsed human CD14 positive cell" prepared by pulse-culturing human peripheral blood CD14 positive cells and NKT cell ligand RK-163 for various times. The NKT cell activation ability (IFN-γ production inducing potency), recovery rate, and survival rate of human CD14 positive cells pulsed with α-GalCer were compared.

CD14 positive cells immediately after separation of anti-CD14 antibody-bound microbeads were separated, pulse-cultured in a medium containing NKT ligand RK-163 or other NKT cell ligand α-GalCer at 100 ng/mL and GM-CSF (53.3 ng/mL) for various times (0, 16, 48, 64 and 72 hr), and an influence on the activity of NKT cells to induce IFN-γ production was compared. As a result, IFN-γ production inducing activity was found from 16 hr after pulsing and high activity was found 48-72 hr later (FIG. 4, left). The recovery rate and survival rate at that time were highest at 48 hrs (FIG. 4, right). Thus, 48 hours after RK-163 pulsing is a good condition for all of NKT cell activating ability (IFN-γ production induction), recovery rate, survival rate of CD14 positive cells immediately after separation of anti-CD14 antibody-bound microbeads (FIG. 4).

Figure 5:
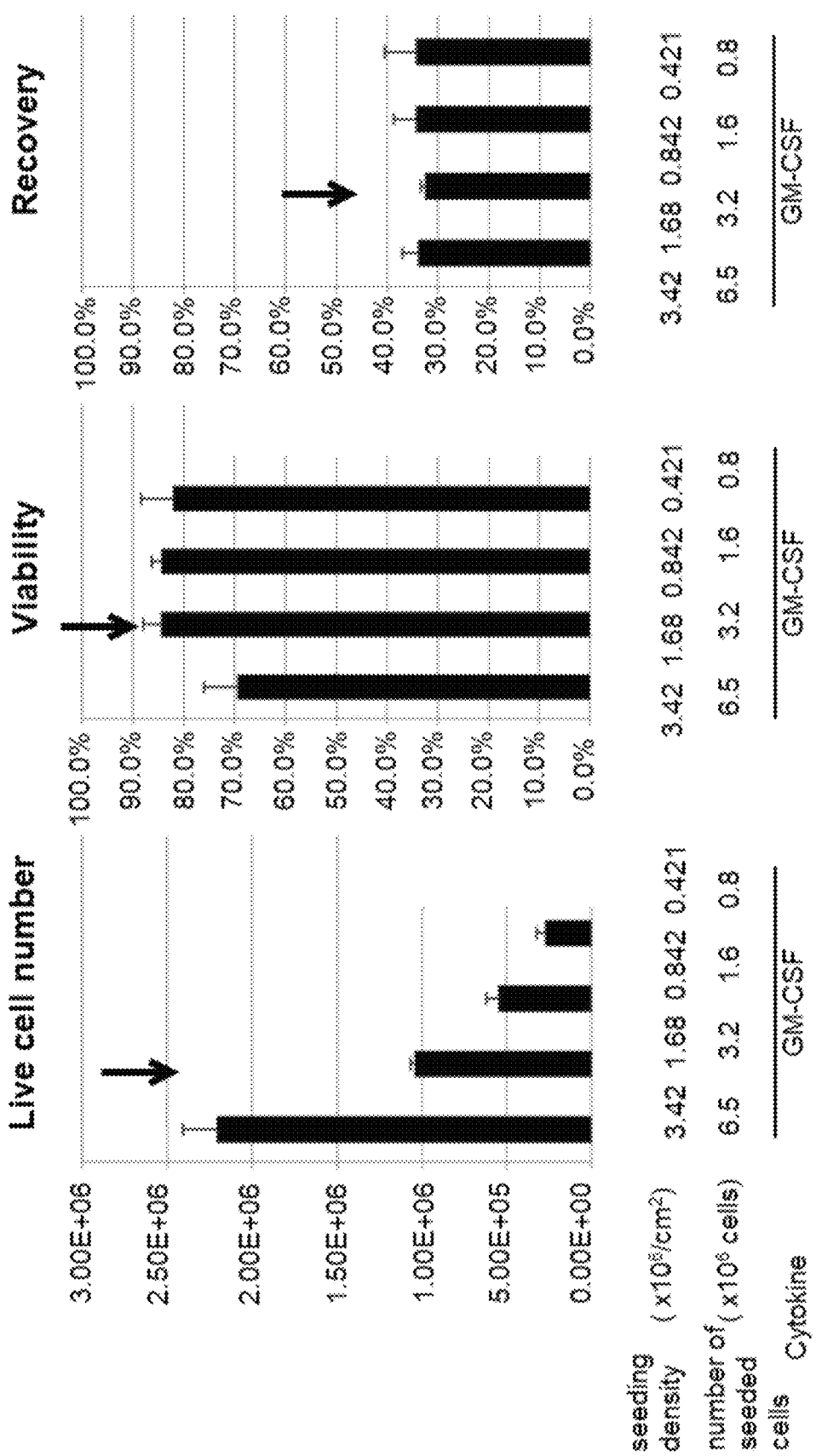
FIG. 5 shows viable cell number, survival rate and recovery rate of RK-163-pulsed human CD14 positive cells obtained by culturing human peripheral blood CD14 positive cells and RK-163 for 48 hr at various seeding densities in a GM-CSF-containing medium.

(5) The cell concentration affording the most efficient RK-163-pulsed CD14 positive cells was studied by RK-163 pulse culture of CD14 positive cells (monocytes), isolated from human peripheral blood, for 2 days in the presence of Recombinant Human GM-CSF (53.3 ng/mL) and RK-163 (100 ng/mL). To be specific, CD14 positive cells isolated from human peripheral blood were suspended at various cell densities ($0.42-3.42\times10^6$/cm$^2$) in AIM-V medium, seeded in a 24-well plate, cultured at 37° C., 5% CO$_2$ for 48 hr, and number of viable cells, survival rate and recovery rate were evaluated (FIG. 5).

(6) Study of Influence of α-GalCer or RK-163-Pulsed Human CD14 Positive Cell and α-GalCer or RK-163-Pulsed Human Dendritic Cell on Proliferation Ability of NKT Cells Human NKT cells were stimulated by culturing for 8-10 days with the "α-GalCer or RK-163-pulsed human CD14 positive cell" or "α-GalCer or RK-163-pulsed human dendritic cell" produced in the same manner as above in a mixed medium of AIM-V (50%) and RPMI-1640 (45%) and containing FCS (5%) (Sigma, lot 14K525), sodium pyruvate, NEAA (non-essential amino acid), 2-ME, IL-2 (100 U/mL) (Imunace), and proliferation activity of NKT cells was measured. The mixing ratio of NKT cells and RK-163-pulsed CD14 positive cells or RK-163-pulsed dendritic cells was set to 1:1.5-5.

Figure 6:
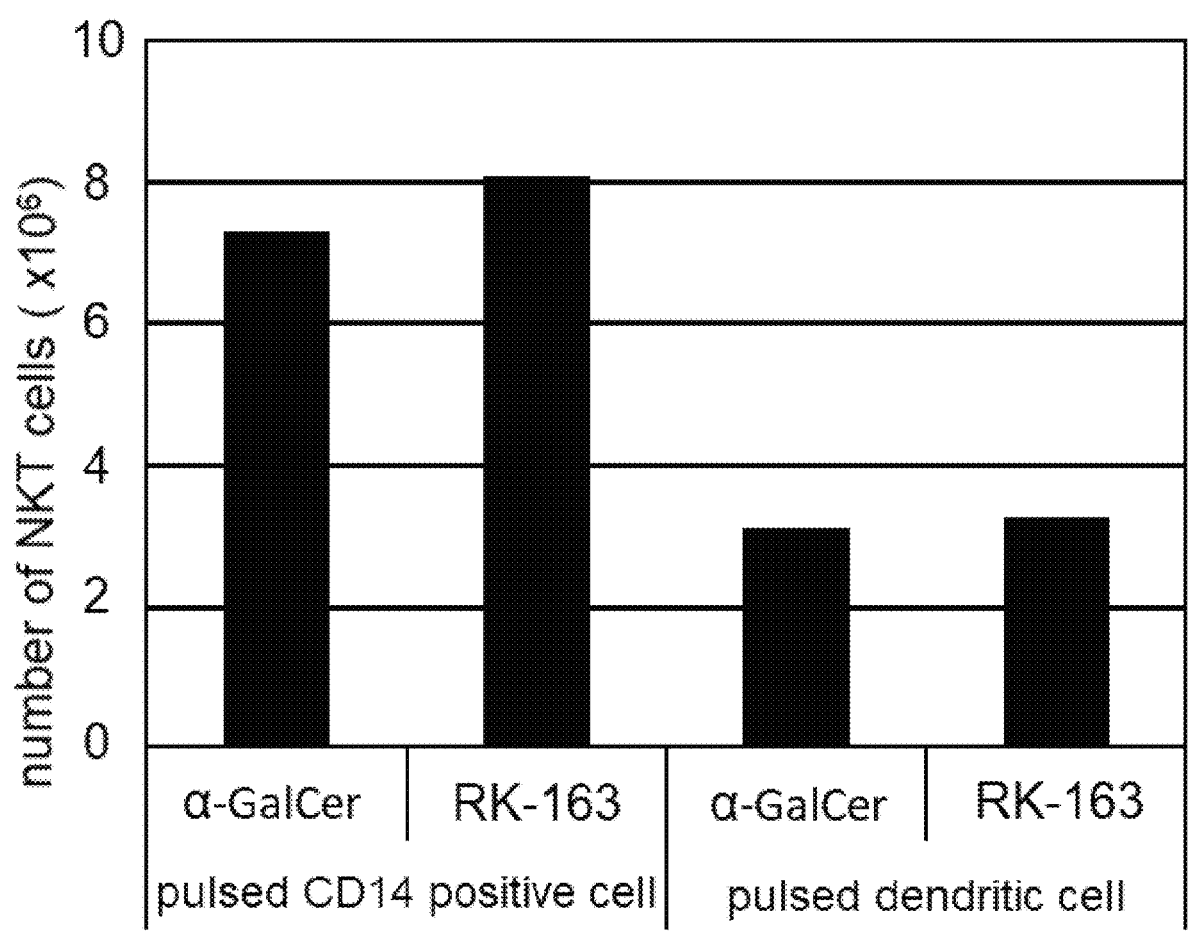
FIG. 6 shows comparison results of the ability of "α-GalCer or RK-163-pulsed human CD14 positive cell" and "α-GalCer or RK-163-pulsed human dendritic cell" to induce proliferation of NKT cells.

As a result, it was shown that RK-163 or α-GalCer-pulsed CD14 positive cell induce proliferation of NKT cells far more strongly than RK-163 or α-GalCe-pulsed dendritic cell. Furthermore, no particular difference in the NKT cell proliferation induction activity was found between α-GalCer-pulsed CD14 positive cell and RK-163-pulsed CD14 positive cell (FIG. 6).

(7) Study of Influence of RK-163-Pulsed Human CD14 Positive Cell and RK-163-Pulsed Human Dendritic Cell on Cytotoxic Ability of NKT Cells Human NKT cells were stimulated by culturing for 8-10 days with the "RK-163-pulsed human CD14 positive cell" or "RK-163-pulsed human dendritic cell" produced in the same manner as above in a mixed medium of AIM-V (50%) and RPMI-1640 (45%) and containing FCS (5%) (lot suitable for proliferation of iPS cells), sodium pyruvate, NEAA, 2-ME, IL-2 (100 U/mL) (Imunace). The mixing ratio of NKT cells and RK-163-pulsed CD14 positive cells or RK-163-pulsed dendritic cells was set to 1:1.5-5. The obtained human NKT cells were cultured for 4 hr together with NCI H460 cells (human lung cancer cell line) in an FBS (10%)-containing complete RPMI-1640 medium on a 96 well round-bottomed plate and the cytotoxic activity against NCI H460 cells was examined. The number of the target cells (NCI H460 cells) was set to $1\times10^4$ cells/well and the effector:target ratio was set to 3:1 and 10:1.

Figure 7:
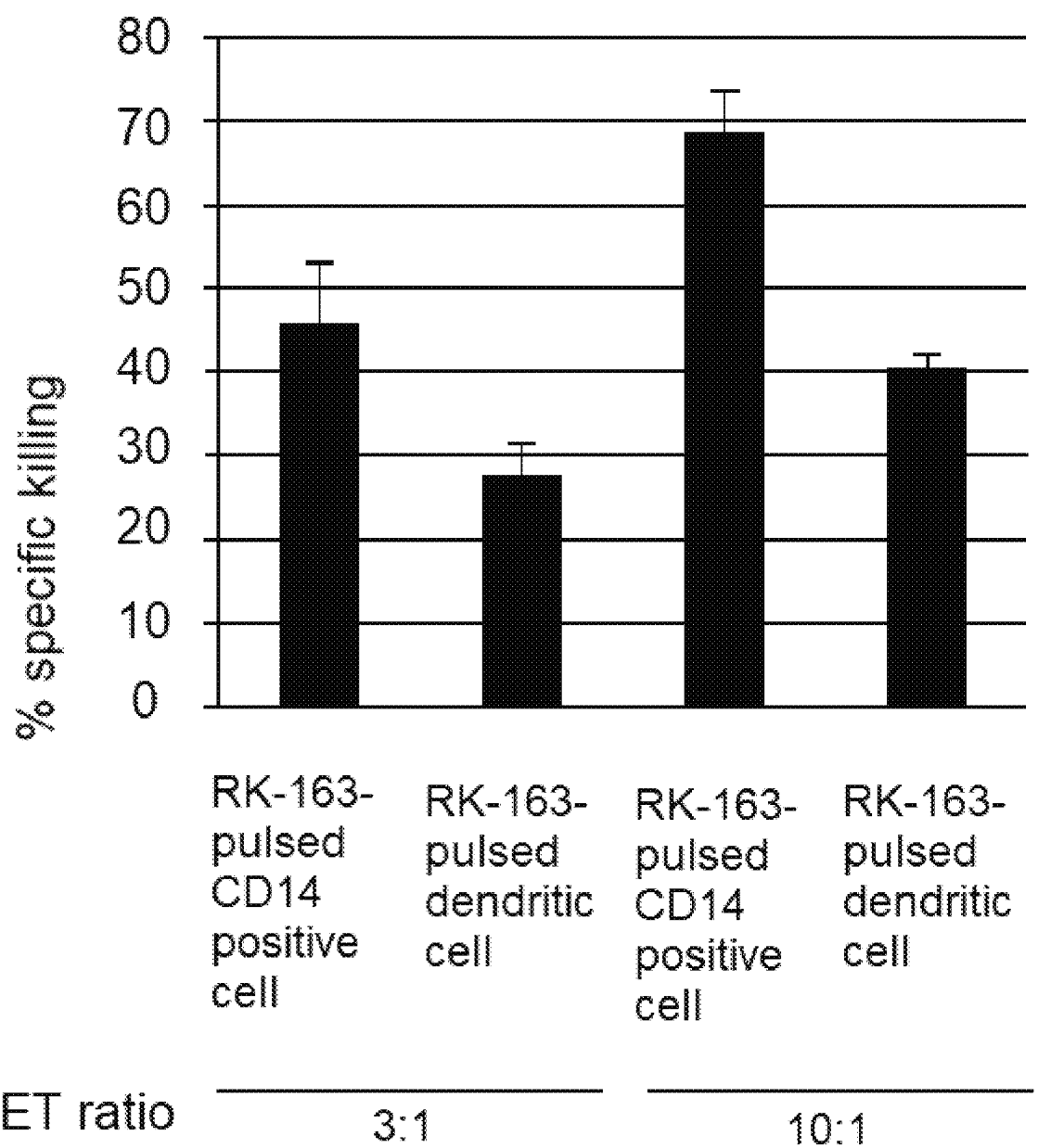
FIG. 7 shows comparison results of the ability of "RK-163-pulsed human CD14 positive cell" prepared from human peripheral blood CD14 positive cells and "RK-163-pulsed human dendritic cell" to induce cytotoxic activity of NKT cells.

As a result, it was shown that human NKT cells obtained by co-culturing human NKT cells with "RK-163-pulsed human CD14 positive cell" have stronger cytotoxic activity than human NKT cells obtained by co-culturing with "RK-163-pulsed human dendritic cell" (FIG. 7). In addition, RK-163 was found to induce stronger cytotoxic activity on human NKT cells as compared to α-GalCer.

(8) Study of NKT Cell Activating Ability (IFN-γ Production Induction) of "NKT Cell Ligand-Pulsed CD14 Positive Cell" Obtained by Pulse Culture with Various NKT Cell Ligands (RCAI-85, RCAI-137, RK-163)

Figure 8:
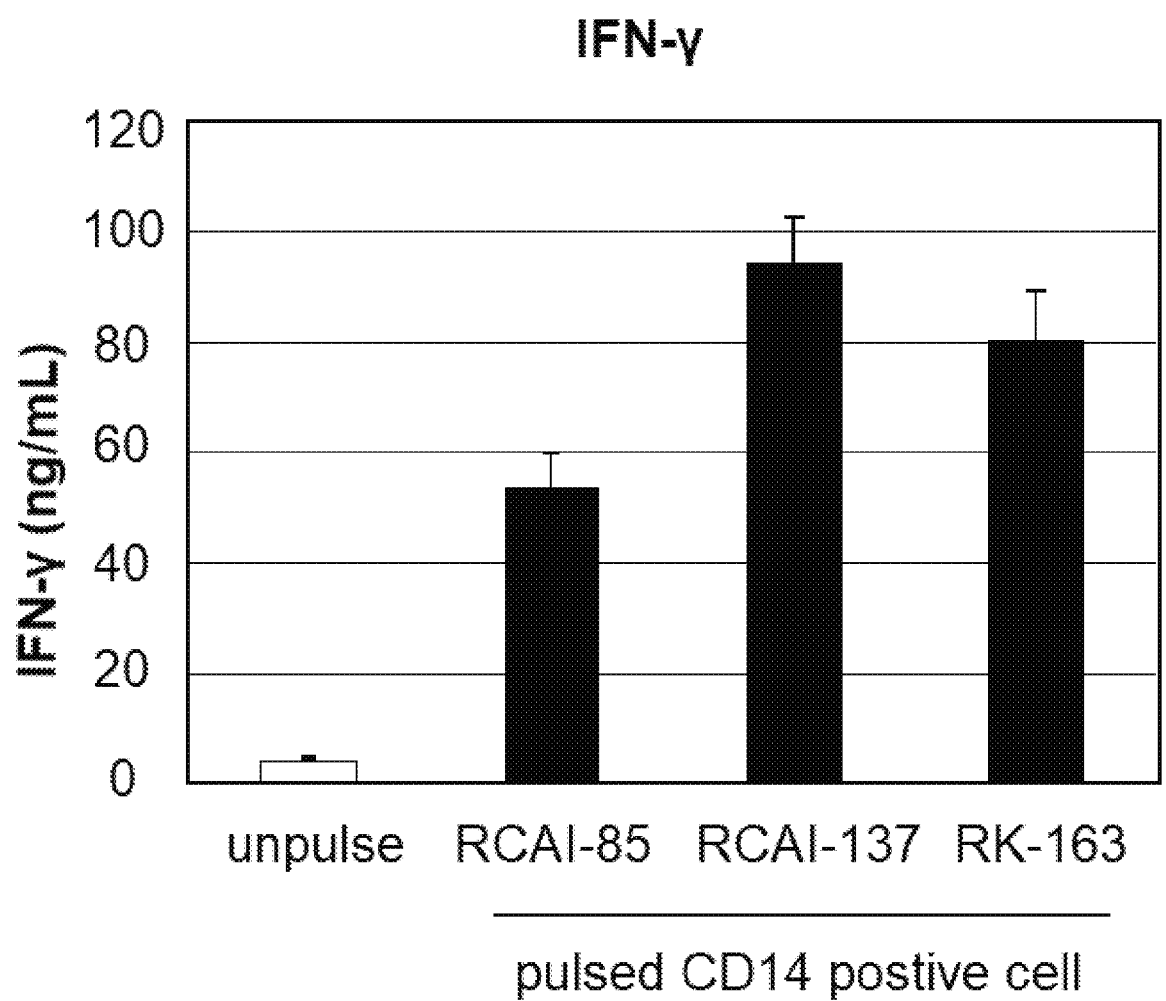
FIG. 8 shows the NKT cell activation (IFN-γ production inducing) ability of "NKT cell ligand-pulsed human CD14 positive cell" obtained by culturing human peripheral blood CD14 positive cells with various NKT cell ligands (RCAI-85, RCAI-137, RK-163) for 48 hr in the presence of GM-CSF.

Using RCAI-85 (100 ng/mL), RCAI-137 (100 ng/mL) instead of RK-163, CD14 positive cells (monocytes) isolated from human peripheral blood were pulsed for 48 hr to give each ligand-pulsed CD14 positive cell. $1\times10^5$ RK-163-pulsed CD14 positive cells or other ligand-pulsed CD14 positive cells were seeded in a 96 well round-bottomed plate, and cocultured with $1\times10^5$ human NKT cells for 48 hr in a 10% FBS-containing complete RPMI-1640 medium, and the concentration of IFN-γ in the culture medium was measured. As a result, it was shown that RK-163-pulsed CD14 positive cell and other ligand-pulsed CD14 positive cell strongly induce IFN-γ production from NKT cells, like RK-163-pulsed CD14 positive cell (FIG. 8).

(9) Study of In Vivo Antitumor Action of "RK-163-Pulsed Human CD14 Positive Cell"

It was verified that "RK-163-pulsed human CD14 positive cell" actually shows an antitumor effect in a tumor-bearing animal.

B16 mouse melanoma cells were transplanted into the spleen of C57BL/6 female mouse, and "RK-163-pulsed human CD14 positive cell" prepared according to the method of. Example 1 was intravenously administered 4 days later. The mouse was euthanized 10 days later, the liver was isolated, a homogenate thereof was prepared and dissolved in 1N NaOH, and the supernatant was recovered. The absorbance of melanin dye in the supernatant was measured by a spectrophotometer, an analytical curve was plotted and the number of tumor cells metastasized from the spleen into the liver was quantified.

Figure 9:
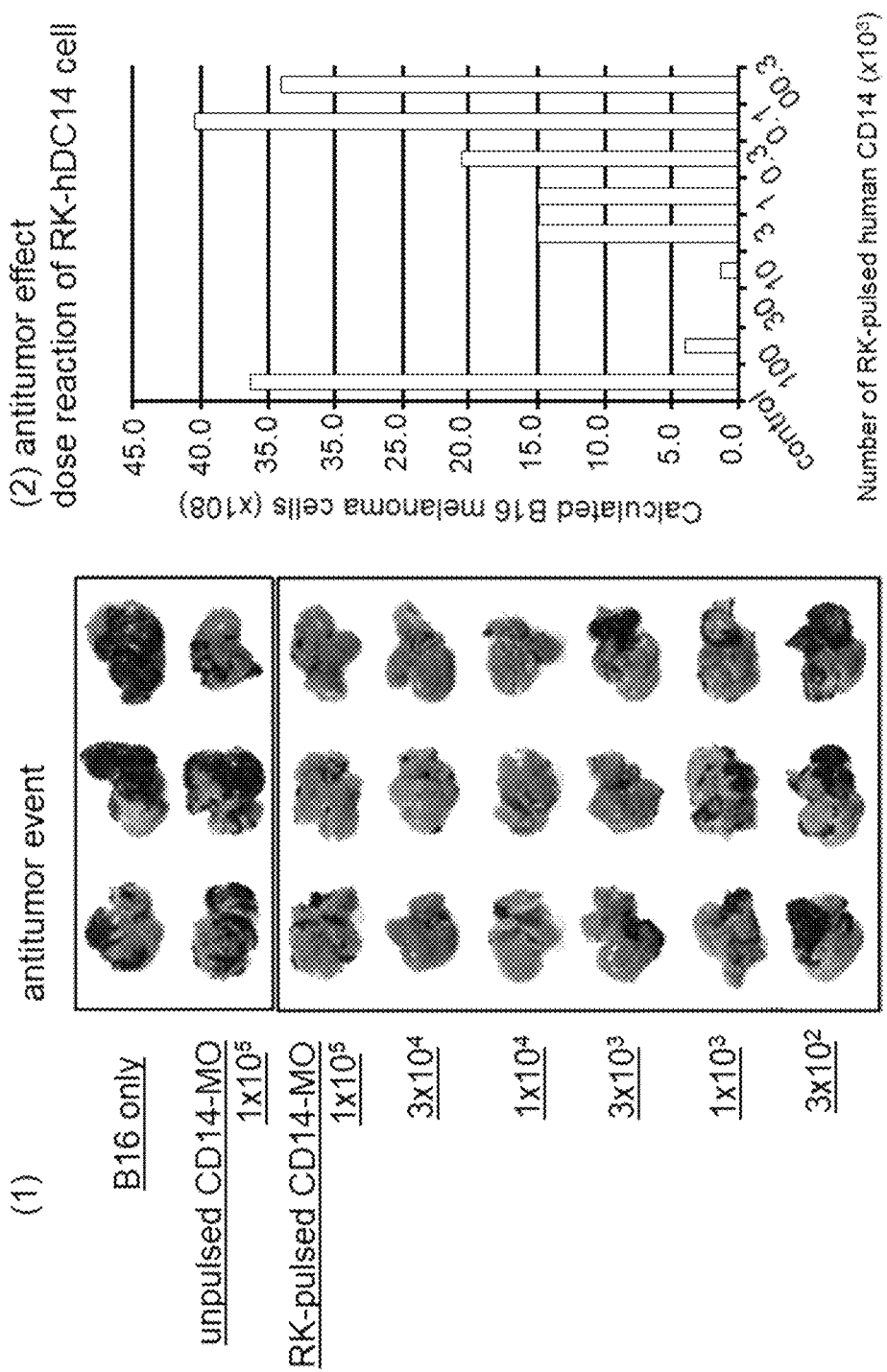
FIG. 9 shows antitumor effect of "RK-163-pulsed human CD14 positive cell" derived from human peripheral blood.

As a result, "RK-163-pulsed human CD14 positive cell" showed a strong antitumor effect and the remarkably suppressed metastasis of melanoma tumor cells (FIG. 9).

Example 2

1. Material and Method
1) Starting material 1: human-derived CD14 positive cell line (here typically, THP-1 cell, U9375 cell, CD14 positive cell line induced from human iPS cell (hereinafter to be referred to as human iPS-CD14 positive cell line) was used).

THP-1 cell and U937 cell were obtained from ECACC, JCRB. The iPS-CD14 positive cell line used was a cell established by Mr. Senju of Kumamoto University (Senju et al. Stem Cells, 27:1021-1031, 2009).

2) Production of Antigen Presenting Cell for NKT Cell Activation Using Human-Derived CD14 Positive Cell Line Human CD14 positive cell line THP-1 cells and U937 cells were suspended in RPMI1640/10% FBS culture medium to $1-3\times10^6$ cells/ml, and seeded in a 24-well culture plate (Falcon) at a cell density of 1 mL/well. Simultaneously, RK-163 (bulk powder was dissolved in PBS added with DMSO and 0.5% Tween 20) was added to a final concentration 100 ng/mL, and the cells were cultured at 37° C., 5%

$CO_2$ for 8-48 hr in the absence of GM-CSF to give "RK-163-pulsed human CD14 positive cell line".

iPS-CD14 positive cells were cultured for 8-48 hr in the presence of RK-163 in the same manner as for THP-1 and U937 to give "RK-163-pulsed human iPS-CD14 positive cell line".

3) Analysis Method (1) Calculation Method of Viable Cell Number and Survival Rate After staining with 0.4% Trypan Blue (Bio-Rad), unstained viable cells and blue-stained dead cells were measured twice with TC20™ Automated Cell Counter (Bio-Rad). The average thereof was calculated and the viable cell number and survival rate were calculated.

(2) Fluorescence Activated Cell Sorting (FACS) Analysis Method

Phycoerythrin-labeled anti-human antibody against each of the following antigens [CD14 (clone HCD14, Biolegend), CD11c (clone 3.9, Biolegend), CD11b (clone ICRF44, BD Biosciences), CD45 (clone HI30, Biolegend), HLA-DR (clone L243, Biolegend), CD1d (clone 51.1, Biolegend), CD40 (clone 5C3, Biolegend), CD95(Fas) (clone DX2, Biolegend), 20, CD80 (clone 2D10, Biolegend), CD86 (clone IT2.2, Biolegend), and CD209 (clone DC-SIGN, Miltenyi Biotech)] was added to the cells, and static reaction was performed under shading for 30 min at 4° C. After centrifugation and washing, the cells were suspended in 0.5% human serum albumin-added PBS, and the purity of CD14 positive cells and expression of various surface antigens were examined by a flow cytometer (FACSCantoII, BD Biosciences).

(3) Measurement of NKT Cell Activating Action (IFN-γ Production)

Any of human-derived CD14 positive cell lines (THP-1, U937, and human-derived iPS-CD14 positive cell were used here) and NKT cell ligand RK-163 were cultured for 8-48 hr in the presence or absence of GM-CSF to prepare "RK-163-pulsed human CD14 positive cell line". After culturing, the recovered cells were washed twice by centrifugation, and the number of viable cells after Trypan Blue staining was calculated by TC20™ Automated Cell Counter. RK-163-pulsed cells and human NKT cell line were respectively suspended in 10% fetal bovine serum (Sigma, Lot No. 114K525)-added RMPI-1640 (Invitrogen) to $1 \times 10^6$/mL, each cell suspension was seeded at a cell concentration of $1 \times 10^5$/0.1 mL/well in a 96-well round-bottomed culture plate, and the cells were cultured at 37° C., 5% $CO_2$ for 48 hr. After culturing, 200 μL of supernatant was recovered, and the produced and secreted IFN-γ was measured using a commercially available ELISA kit (BD Biosciences).

2. Results and Discussion (1) Surface Antigen Expression Patterns of Human-Derived CD14 Positive Cell Line (THP-1, U937, and Human-Derived iPS-CD14 Positive Cell Were Used)

The surface antigen expression patterns of THP-1, U937, and human-derived iPS-CD14 positive cell are respectively shown in FIGS. 10-1, 10-2 and 10-3. In NKT cell ligand-pulsed THP-1 cell and iPS-CD14 positive cell, expression of CD1d molecule essential for antigen presentation of NKT ligand and expression of CD40 molecule essential for NKT cell activation were found by FACS analysis. In U937 cell, expression of CD1d was also found by FACS analysis, and expression of CD40 mRNA increased after RK-163 pulsing. Therefore, it is shown that not only the human peripheral blood-derived CD14 positive cell described in Example 1 but also CD14 positive cell line can efficiently activate NKT cells.

(2) Comparison of IFN-γ Production Induction Potency (NKT Cell Activating Action) of "RK-163-Pulsed Human CD14 Positive Cell Lines" (THP-1, U937, and Human-Derived iPS-CD14 Positive Cell were Used)

Figure 11:
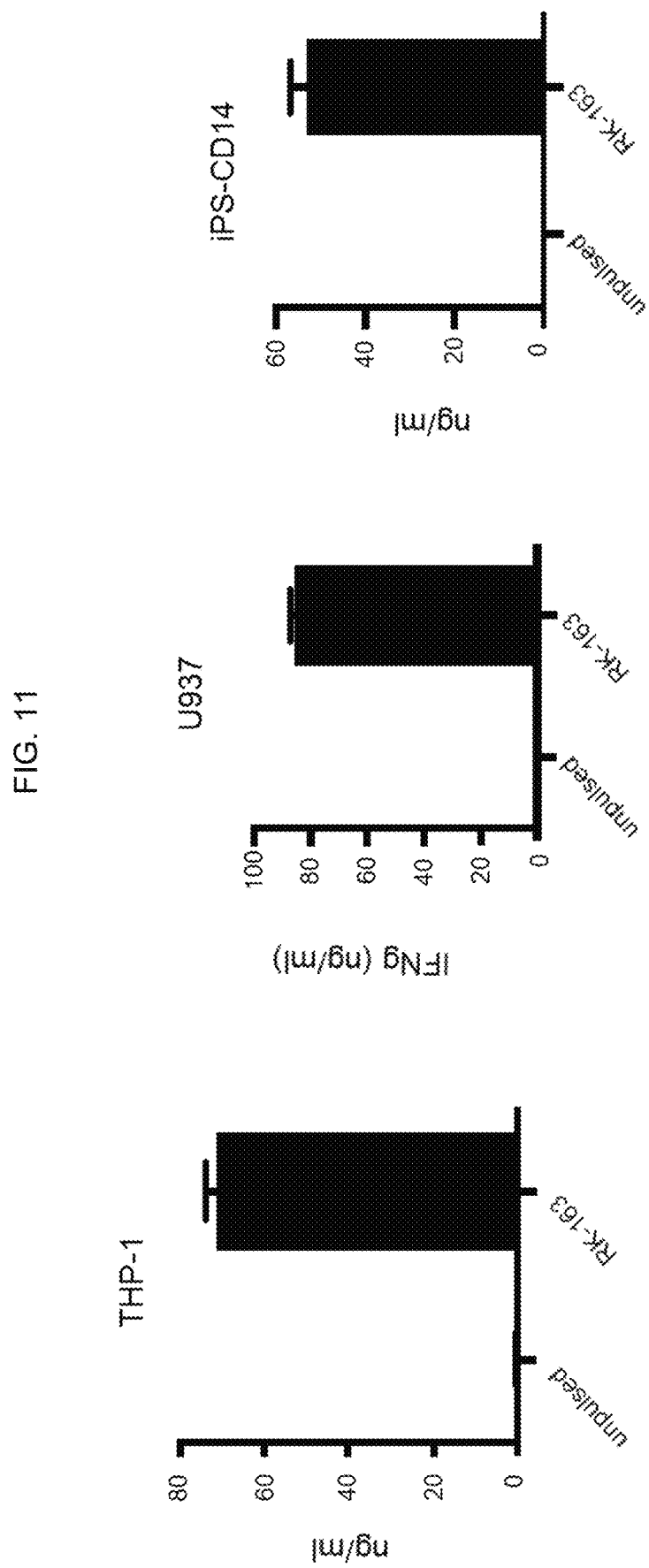
FIG. 11 shows IFN-γ production inducing effect on human NKT cell line by human THP-1, U937 and human iPS-CD14 positive cell line, each pulsed with RK-163.

Human NKT cell line was cocultured with each "RK-163-pulsed human CD14 positive cell line", and IFN-γ production of each human NKT cell line was examined. Similar to the "RK-163-pulsed human CD14 positive cell" prepared from human peripheral blood CD14 positive cell, it was shown that "RK-163-pulsed human CD14 positive cell line" also has a high NKT cell activating action (FIG. 11).

(3) Influence of RK-163 Pulse Time on IFN-γ Production Induction Potency (NKT Cell Activating Action) in Preparing "RK-163-Pulsed Human Derived from CD14 Positive Cell Line"

Human-derived CD14 positive cell line (U937 cells) was pulse-cultured in the presence or absence of NKT ligands RK-163 (100 ng/mL) and GM-CSF for various times (2-48 hr), and an influence on the activity of NKT cells to induce IFN-γ production was compared. As a result, IFN-γ production inducing activity was found from 2 hr after pulsing (FIG. 12, left).

In addition, THP-1 was pulse-cultured with RK-163 (100 ng/mL) in the absence of GM-CSF for 8-24 hr, $3 \times 10^5$ cells of "RK-163-pulsed THP-1 cell line" were intravenously injected to C57BL/6 mouse, blood samples were collected after 24 hr and blood IFN-γ concentration was quantified to find an increase in the blood IFN-γ concentration from 7 hr after pulsing (FIG. 12, right).

From the above results, it was clarified that a cell line expressing CD14 and CD1d, like THP-1, U937, can induce IFN-γ production of NKT cells with a very short pulse treatment even in the absence of GM-CSF.

(4) Influence of RK-163-Pulsed Human-Derived CD14 Positive Cell Line (THP-1 and Human-Derived iPS-CD14 Positive Cell Line were Used Here) on Cytotoxic Activity of NKT Cells In the same manner as in Example 1(7), an influence on the cytotoxic activity of human NKT cells was studied. That is, human NKT cells were stimulated by culturing with "RK-163-pulsed human-derived CD14 positive cell line" at a mixing ratio of "1:1.5-5" for 16-24 hr. The obtained human NKT cell line was cultured for 4 hr together with NCI H460 cells (human lung cancer cell line) or YAC-1 cells (mouse lymphoma-derived cells) in an FBS (10%)-containing complete RPMI-1640 medium on a 96 well round-bottomed plate and the cytotoxic activity against NCI H460 cells or YAC-1 cells was examined. The number of the target cells (NCI H460 cells or YAC-1) was set to $1 \times 10^4$ cells/well and the effector:target ratio was set to 3:1 and 10:1.

Figure 13:
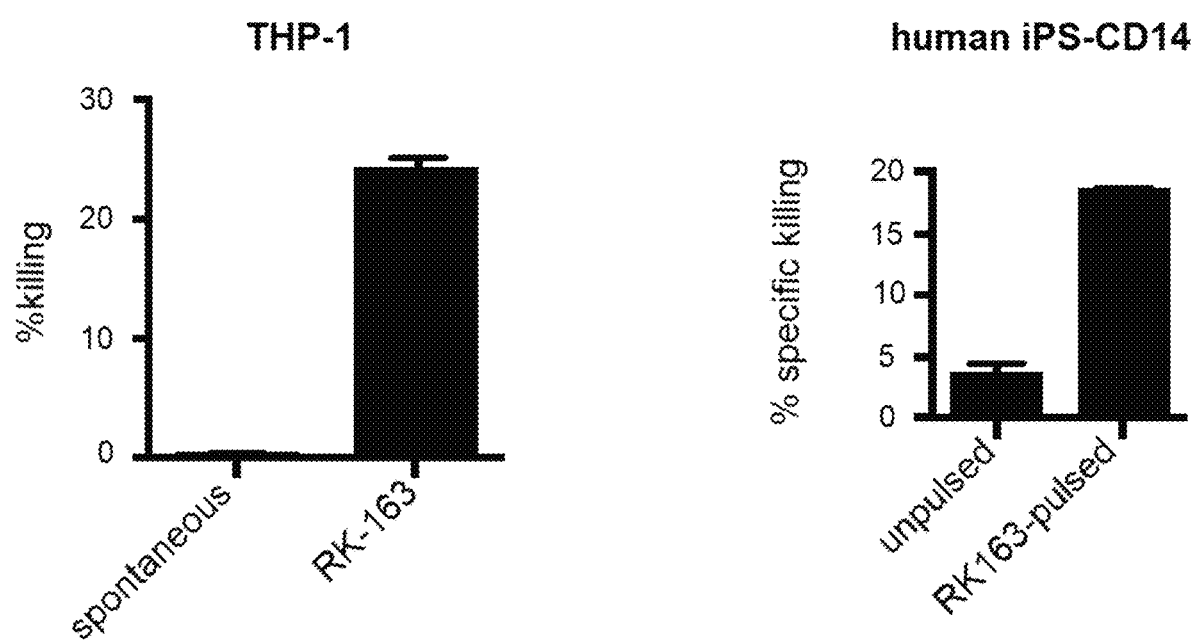
FIG. 13 shows induction of cytotoxic activity of NKT cells by RK-163-pulsed human CD14 positive cell line (THP-1, iPS-CD14 positive cell line).

As a result, the cytotoxic activity of NKT cells was induced even when the "RK-163-pulsed human derived from CD14 positive cell line" was used (FIG. 13).

(5) Study of In Vivo Antitumor Action of "RK-163 or α-GalCer-Pulsed Mouse Dendritic Cell" and "RK-163-Pulsed Human CD14 Positive Cell Line"

It was verified that "RK-163 or α-GalCer-pulsed mouse dendritic cell" and "RK-163-pulsed human CD14 positive cell line" actually show an antitumor effect in a tumor-bearing animal.

B16 mouse melanoma cells were transplanted into the spleen of C57BL/6 female mouse, and RK-163 or α-GalCer-pulsed mouse dendritic cells (derived from C57BL/6) prepared according to the method of Example 1 were intravenously administered 4 days later. The mouse was euthanized 10 days later, the liver was isolated, a homogenate thereof was prepared and dissolved in 1N NaOH, and the supernatant was recovered. The absorbance of melanin dye in the supernatant was measured by a spectrophotometer, an analytical curve was plotted and the number of tumor cells metastasized from the spleen into the liver was quantified.

Figure 14A:
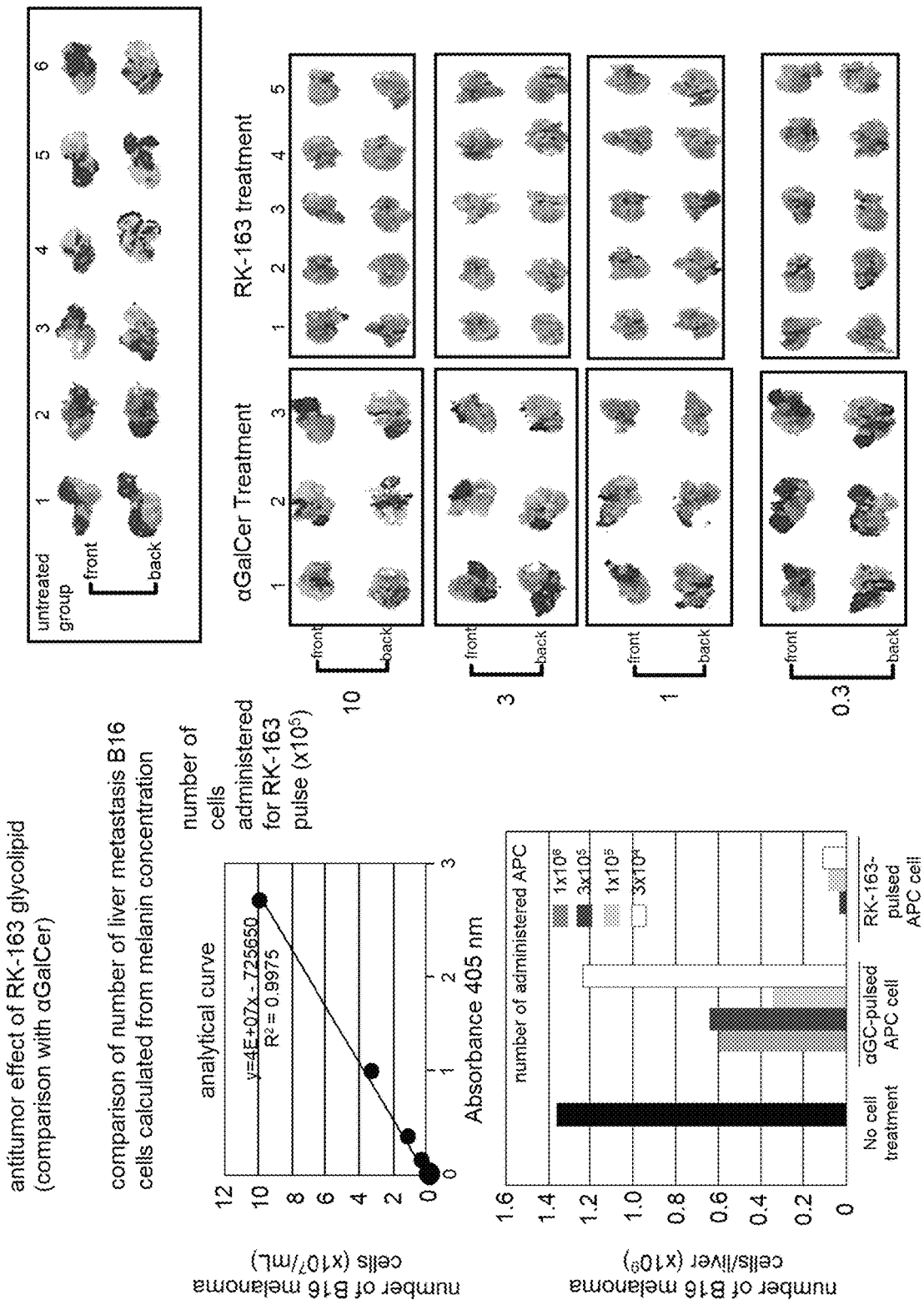
FIG. 14A shows an antitumor effect induced by mouse dendritic cells pulsed with RK-163 or α-GalCer.

As a result, the "RK-163-pulsed mouse dendritic cell" showed a strong antitumor effect compared to the "α-GalCer-pulsed mouse dendritic cell" and the remarkably suppressed metastasis of melanoma tumor cells (FIG. 14A).

Similarly, a strong antitumor effect was also shown in the "RK-163-pulsed human CD14 positive cell line" (THP-1 cells, U937 cells) (FIG. 14B).

(6) Adjuvant Action by RK-163-Pulsed Mouse Dendritic Cell and RK-163-Pulsed Human CD14 Positive Cell Line (THP-1, U937 were Used Here)

The antitumor effect of NKT cells is induced not only by direct action on tumor, but rather, by adjuvant action which activates other immunocompetent cells. It was evaluated whether RK-163-pulsed mouse dendritic cells and RK-163-pulsed human CD14 positive cell line activate NKT cells in the body and activate the innate immune system NK cells by its adjuvant action.

Figure 15A:
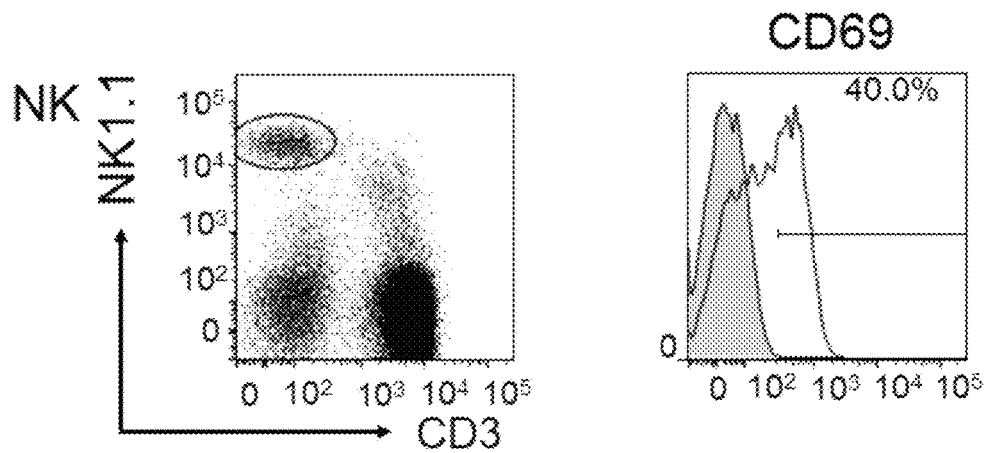
FIG. 15A shows activation of NK cell by an adjuvant action of NKT cells induced by the administration of RK-163-pulsed mouse dendritic cells.

RK-163-pulsed mouse dendritic cells (derived from 057BL/6) were intravenously administered to 057BL/6 mouse. The mouse was euthanized 14 days later, spleen cells were subjected to FACS analysis, and expression of an activation marker (CD69) in the NK cell fraction (NK1.1 positive, TCRβ negative) was examined. As a result, it was confirmed that almost all (100%) NK cells were activated (increased expression of activation marker CD69 molecule) and NKT cells induced a strong adjuvant effect in vivo (FIG. 15A).

In addition, OVA (ovalbumin) antigen was considered as an artificial tumor antigen, OVA-pulsed splenocytes and RK-163-pulsed human CD14 positive cell line (THP-1 or U937) were intravenously administered to C57BL/6 mouse, and OVA reactive T cells and NKT cells in vivo were simultaneously activated. RK-163-pulsed human CD14 positive cell line was administered again 4 days later and FACS analysis was performed 1 week after the administration.

Figure 15B:
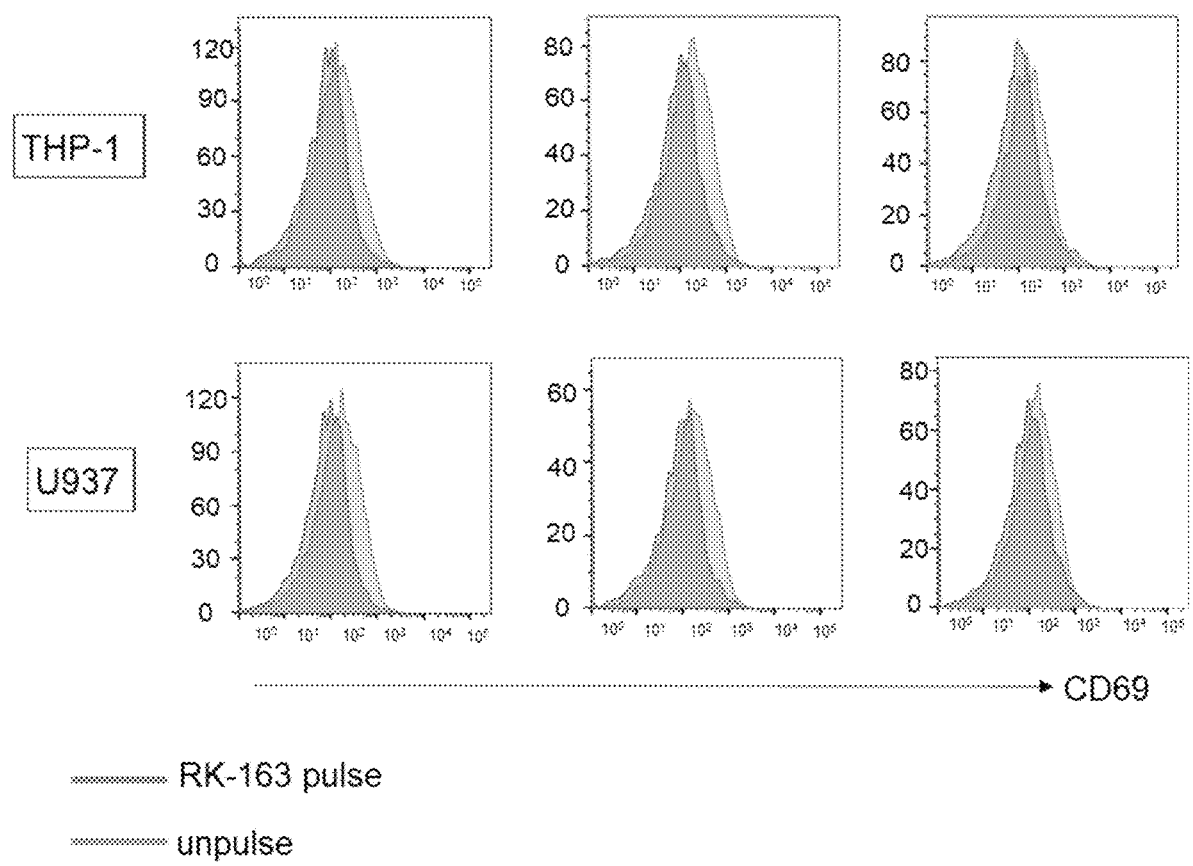
FIG. 15B shows activation of NK cell by an adjuvant action of NKT cells induced by the administration of RK-163-pulsed human CD14 positive cell line.

As a result, it was clarified that the expression of CD69 in the NK cell fraction was also enhanced by the administration of the RK-163-pulsed human CD14/CD1d positive cell line, and the NK cells were activated by the adjuvant effect of NKT cells (FIG. 15B).

Figure 16A:
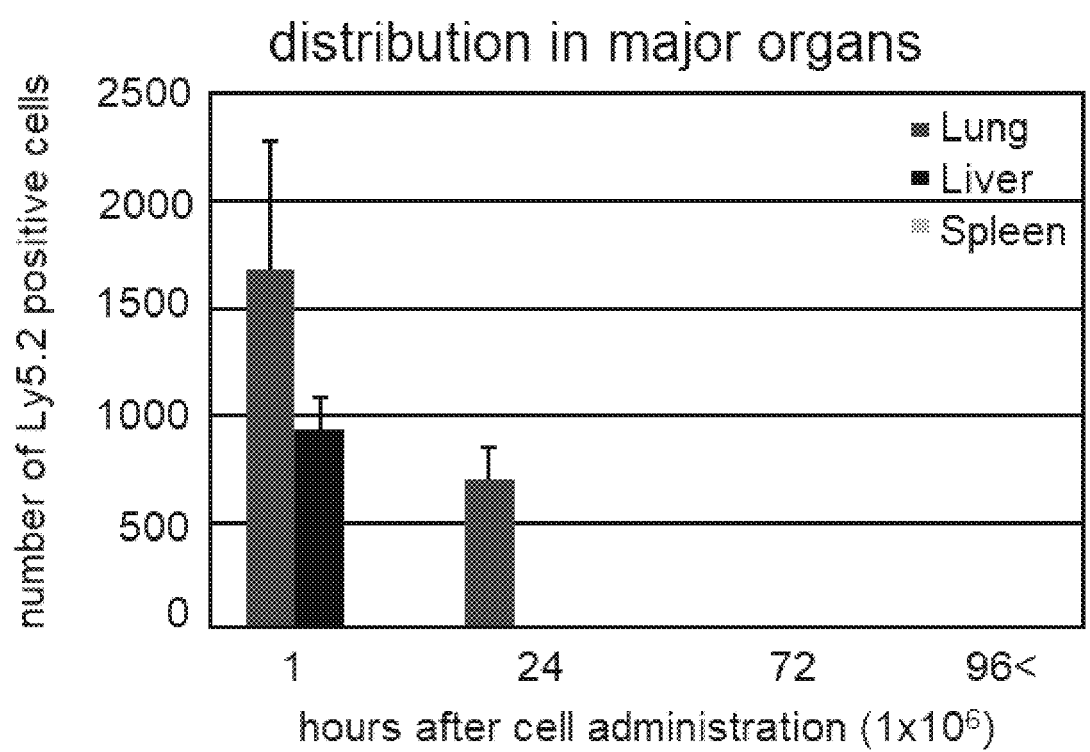
FIG. 16A shows pharmacokinetics of the administered RK-163-pulsed mouse dendritic cells, that they rapidly disappeared from the body.

(7) Cell Dynamics of RK-163-Pulsed Mouse Dendritic Cell and RK-163-Pulsed Human CD14 Positive Cell Line Using B6.CD45.1(Ly.5.1) congenic mouse as a recipient, RK-163-pulsed mouse dendritic cells were intravenously administered and the dynamics of the RK-163-pulsed dendritic cells in the body was examined. As a result, the cells were distributed mainly in the lung and then in the liver 1 hr after the administration, but decreased in 24 hr and observed only in the lung. After 72 hr, the distribution was not observed in any of the organs, and it was clarified that the cells rapidly disappeared from the body (FIG. 16A).

Figure 16B:
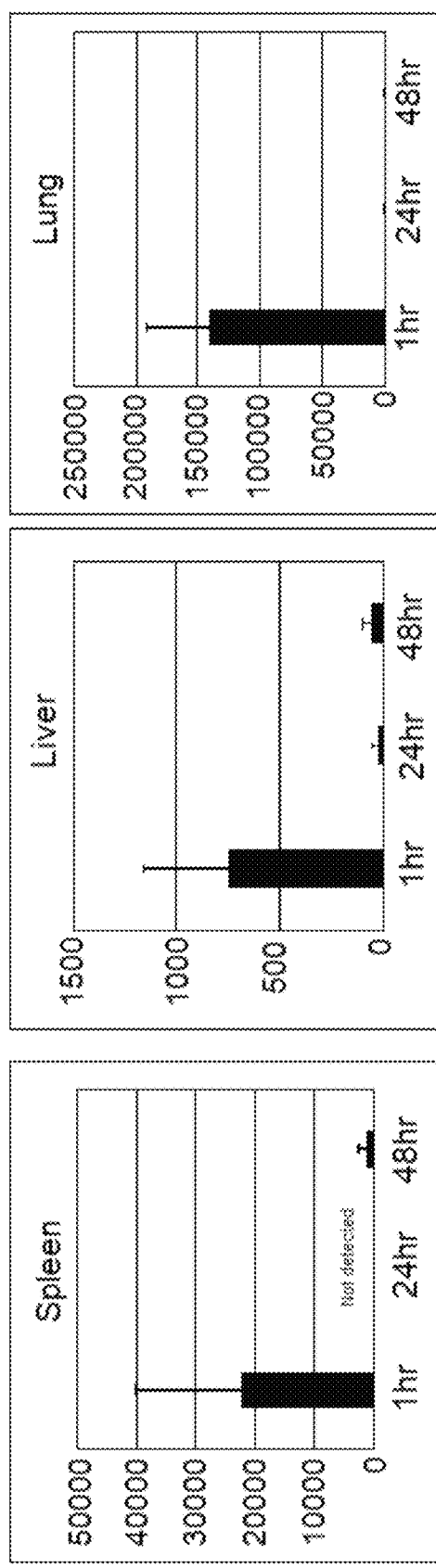
FIG. 16B shows pharmacokinetics of the administered RK-163-pulsed human CD14 positive cell lines, that they rapidly disappeared from the body.

In addition, RK-163-pulsed human CD14 positive cell line (U937 cells here) was intravenously administered to C57BL/6 mouse and the pharmacokinetics was observed. As a result, it was clarified that the cell line was promptly eliminated from the body and was hardly observed in tumor organs after 24 hr and was promptly eliminated from the body (FIG. 16B).

These results suggest that the RK-163-pulsed human CD14 positive cell line can be a highly safe cancer immunocyte therapeutic drug.

(8) Toxicity of RK-163-Pulsed Human CD14 Positive Cell Line

Figure 17A:
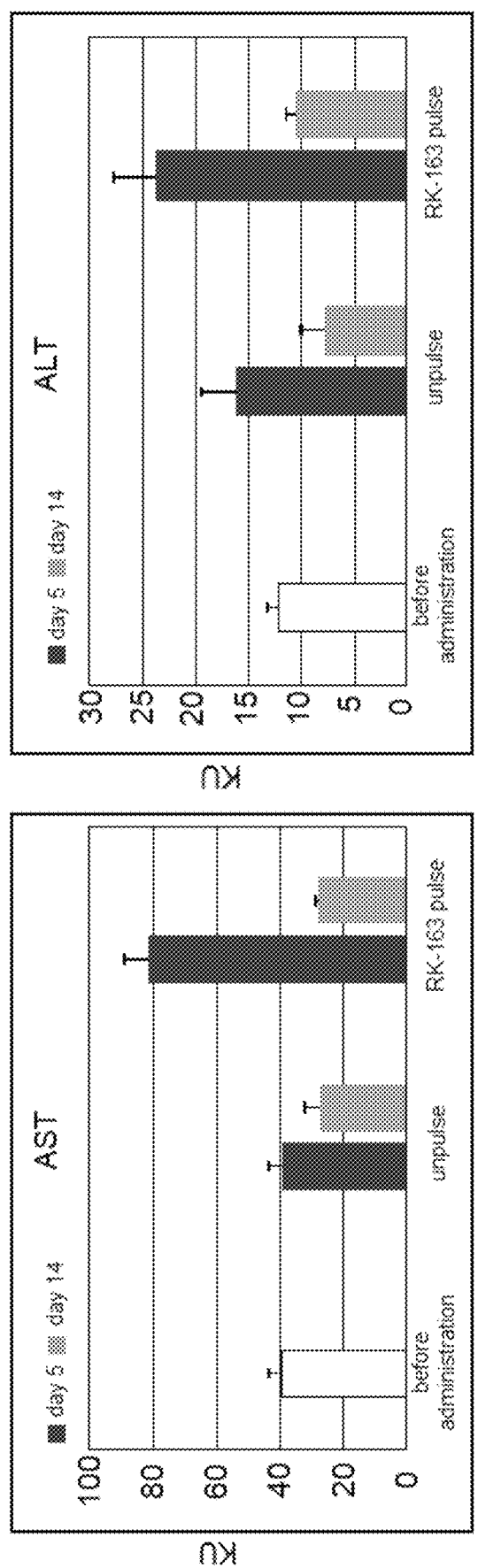
FIG. 17A shows time-course changes of the level of blood acute toxicity markers (AST and ALT) when RK-163-pulsed human CD14 positive cell line was administered.
Figure 17B:
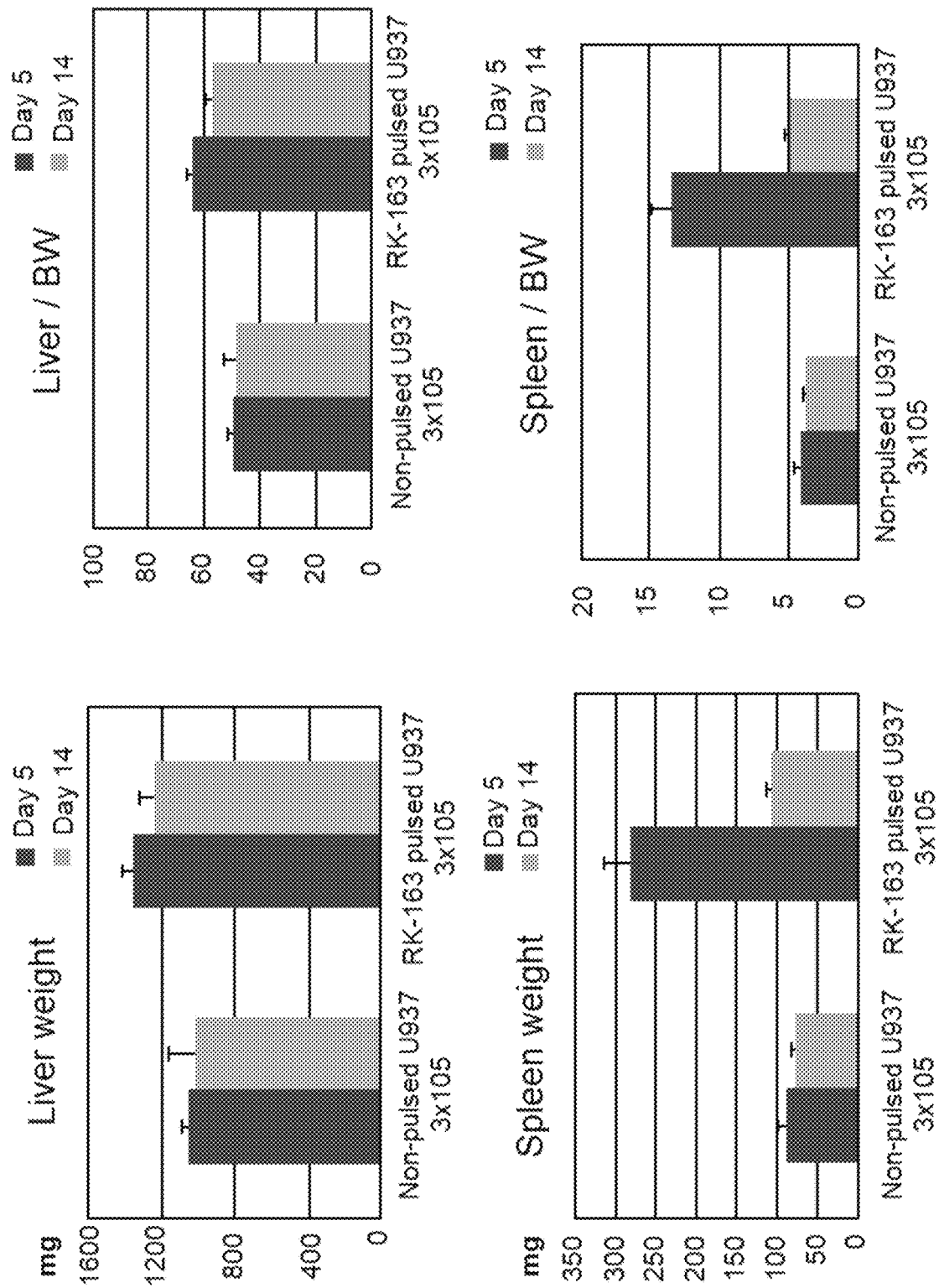
FIG. 17B shows time-course changes of the weight of liver and spleen when RK-163-pulsed human CD14 positive cell line was administered.

To evaluate acute toxicity of RK-163-pulsed human CD14 positive cell line, RK-163-pulsed human CD14 positive cell line (U937 cells here) was intravenously injected once to C57BL/6 mice and acute toxicity up to day 14 was observed. As a result, AST and ALT elevated on day 5 after administration but recovered on day 14 to the state before administration (FIG. 17A). In addition, weight gain of the liver and spleen was observed on day 5 after the administration, but recovered on day 14 to the state before administration (FIG. 17B).

This also suggests that the method of the present invention can be a highly safe treatment method of cancer.

(9) Tumorigenicity of RK-163-Pulsed Human CD14 Positive Cell Line

RK-163-pulsed human CD14 positive cell line (THP-1 or U937 here) is immortalized and can grow infinitely under general culture conditions. That is, when proliferation occurs in the body of an animal, a tumor may be formed. Thus, a tumorigenicity test by a soft agar colony formation method was performed using a sample obtained by irradiating RK-163-pulsed human CD14 positive cell line with radiation to lose proliferative capacity.

Figure 18:
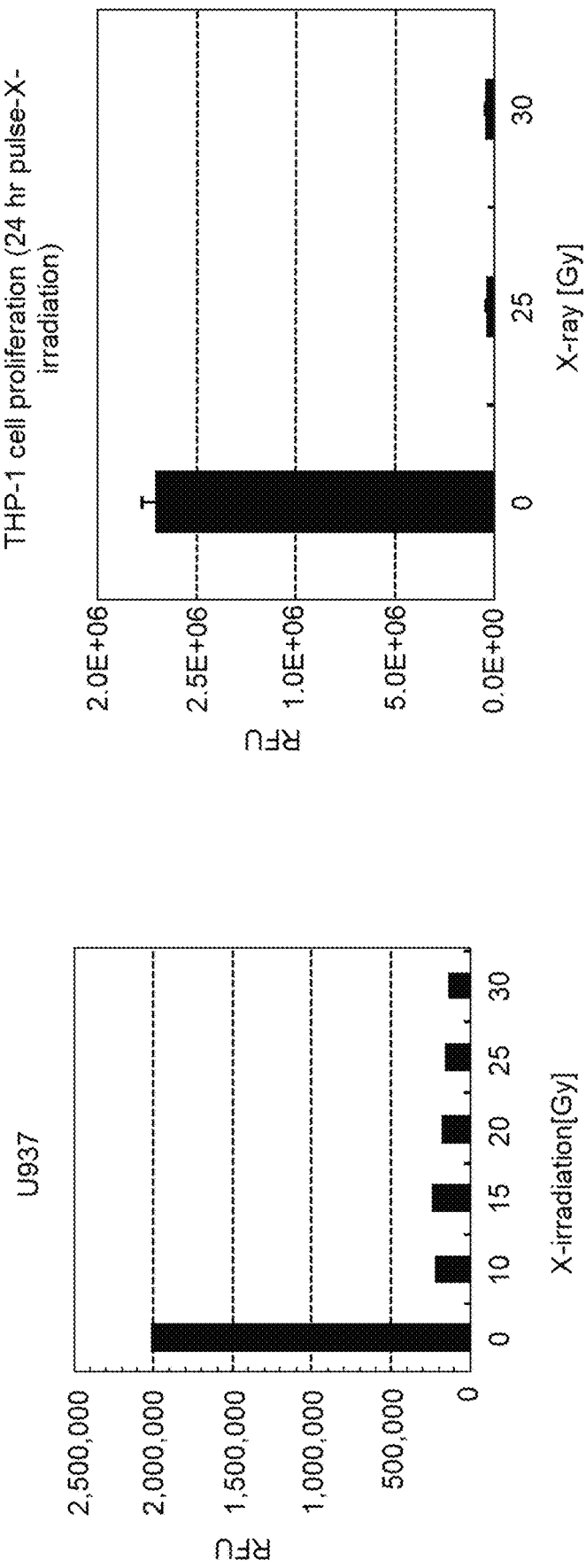
FIG. 18 shows tumorigenicity test results of radiation-irradiated RK-163-pulsed human CD14 positive cell line by a soft agar colony formation method.

Using a soft agar colony formation assay kit (CytoSelect 96 Well Cell Transformation Assay Kit, Cell Biolabs), an experiment was performed according to the experiment procedure manual of the kit. X-ray was irradiated on RK-163-pulsed human CD14 positive cell line (U937 or THP-1), the cell line was seeded on a soft agar, cultured for 8 days and proliferative capacity was measured. As a result, proliferative capacity was not found, and the cell line was shown to be also useful for cancer immunotherapy in the human body without forming a tumor (FIG. 18).

(10) Induction of Long-Term Immune Memory by RK-163-Pulsed Mouse Dendritic Cell and RK-163-Pulsed Human CD14 Positive Cell Line The antitumor effect of NKT cells is exerted not only by direct action by NKT cells but also by adjuvant action which activates other immunocompetent cells. A part of the activated immunocompetent cells remain in the body for a long time to form immune memory. It was verified that the adjuvant action by NKT cells activated by RK-163-pulsed mouse dendritic cell activates antigen-specific CTL and forms long-term memory.

Method:

Ovalbumin (OVA) was considered as an artificial tumor antigen, OVA-pulsed splenocytes and RK-163-pulsed mouse dendritic cells (both derived from C57BL/6) were intravenously administered to C57BL/6 mouse, and OVA reactive T cells and NKT cells in vivo were simultaneously activated. RK-163-pulsed mouse dendritic cells were administered again 4 days later. From one week after the administration, the mouse was euthanized over time, spleen cells were collected, and FACS analysis was performed for the presence of OVA reactive CTL.

Results:

Simultaneous administration of RK-163-pulsed mouse dendritic cell could efficiently induce effector CTL that reacts with OVA and produces IFN-γ. The cellular surface molecules (CD44 and CD62L) of OVA reactive CTL were analyzed. Simultaneous administration of RK-163-pulsed mouse dendritic cell increased both the number of CD44+ CD62L+ Effector Memory CTL and the number of CD44+ CD62L– Central Memory CTL up to 4 weeks, and it was clarified that memory T cells that form immune memory up to 6 months were efficiently induced and maintained (FIG.

19A). Thereafter, it was confirmed that the long-term memory could be maintained up to 9 months.

Figure 19A:
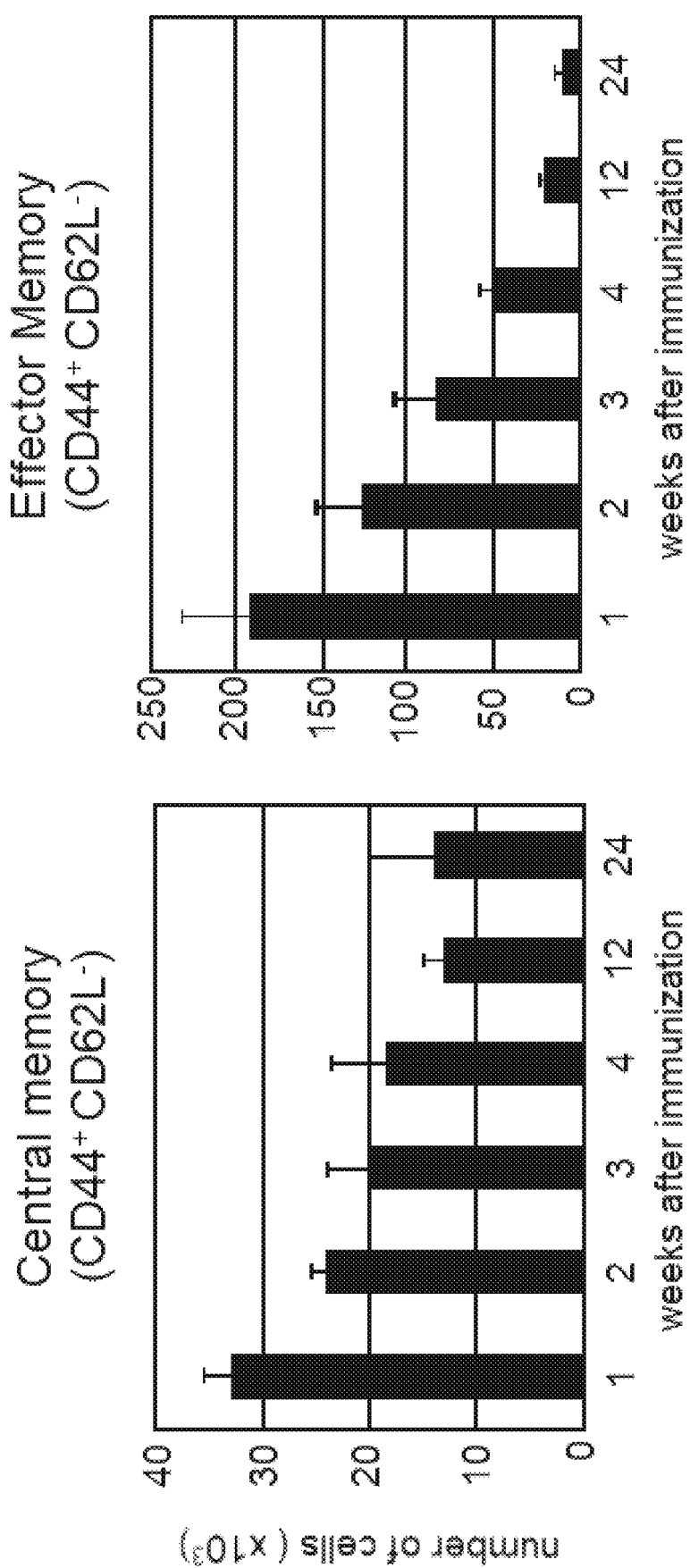
FIG. 19A shows induction of memory T cells by RK-163-pulsed mouse dendritic cells.

Similarly, it was shown that the CD8 memory T cells that form immune memory were induced and maintained in "RK-163-pulsed human-derived CD14 positive cell line" (THP-1 cell, U937 cell) (FIG. 19B).

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the "CLAIMS."

The contents disclosed in any publication cited herein, including patents and patent applications, are hereby incorporated in their entireties by reference, to the extent that they have been disclosed herein.

INDUSTRIAL APPLICABILITY

According to the present invention, an NKT cell ligand-pulsed CD14 positive cell and an NKT cell ligand-pulsed CD14 positive cell line are expected to be produced in a relatively short period. The NKT cell ligand-pulsed CD14 positive cell and an NKT cell ligand-pulsed CD14 positive cell line obtained by the method of the present invention strongly induce proliferation of NKT cells, IFN-γ production and cytotoxic activity of NKT cells. They may therefore be useful as cell preparations for the treatment or prophylaxis of diseases such as cancer, infectious disease and the like.

This application is based on a patent application No. 2016-091674 filed in Japan (filing date: Apr. 28, 2016), the contents of which are incorporated in full herein.

The invention claimed is:

1. A method for producing an NKT cell ligand-pulsed human CD14 positive CD1d positive cell, comprising a step of culturing an isolated CD14 positive CD1d positive cell in a serum free medium containing an NKT cell ligand and GM-CSF at a concentration of 33.3-666.7 ng/mL, wherein the NKT cell ligand is a compound represented by the formula or a salt thereof,
a compound represented by the formula or a salt thereof,
a compound represented by the formula or a salt thereof, or
α GalCer.

2. The method according to claim 1, wherein the cells are cultured at least for 16 hr after addition of the NKT cell ligand.

3. The method according to claim 2, wherein the cells are cultured for 16-72 hr after addition of the NKT cell ligand.

4. The method according to claim 1, wherein a concentration of the NKT cell ligand in the medium is at least 30 ng/ml.

5. An NKT cell ligand-pulsed cell obtained by the method according to claim 1.

6. A cell preparation comprising the cell according to claim 5.

7. An NKT cell activator comprising the cell according to claim 5.

8. An agent for treating melanoma, comprising the cell according to claim 5.

9. A method for activating an NKT cell in a test subject, comprising administering the cell according to claim 5 to the test subject.

10. The method according to claim 9, wherein the test subject is affected with melanoma, or has a history of having cancer or an infectious disease.

11. A method for treating melanoma in a test subject, comprising administering the cell according to claim 5 to the test subject.

12. A method for activating an NKT cell in a test subject, comprising administering the cell preparation according to claim 6 to the test subject.

13. The method according to claim 12, wherein the test subject is affected melanoma, or has a history of having cancer or an infectious disease.

14. A method for treating melanoma in a test subject, comprising administering the cell preparation according to claim 11 to the test subject.

* * * * *

UNITED STATES PATENT AND TRADEMARK OFFICE
CERTIFICATE OF CORRECTION

| | | |
|---|---|---|
| PATENT NO. | : 11,744,860 B2 | Page 1 of 1 |
| APPLICATION NO. | : 16/096561 | |
| DATED | : September 5, 2023 | |
| INVENTOR(S) | : Masaru Taniguchi et al. | |

It is certified that error appears in the above-identified patent and that said Letters Patent is hereby corrected as shown below:

In the Claims

In Claim 13, Column 42, Line 61, "affected melanoma" should read "affected with melanoma"

Signed and Sealed this
Twenty-seventh Day of February, 2024

Katherine Kelly Vidal
*Director of the United States Patent and Trademark Office*